United States Patent
Durkin et al.

(10) Patent No.: US 8,014,569 B2
(45) Date of Patent: Sep. 6, 2011

(54) METHOD AND APPARATUS FOR PERFORMING QUALITATIVE AND QUANTITATIVE ANALYSIS OF PRODUCE (FRUIT, VEGETABLES) USING SPATIALLY STRUCTURED ILLUMINATION

(75) Inventors: Anthony J. Durkin, Irvine, CA (US); David Cuccia, Costa Mesa, CA (US); Frederic Bevilacqua, Paris (FR); Bruce J. Tromberg, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 940 days.

(21) Appl. No.: 11/927,396

(22) Filed: Oct. 29, 2007

(65) Prior Publication Data
US 2008/0101657 A1 May 1, 2008

Related U.S. Application Data

(60) Provisional application No. 60/855,526, filed on Oct. 30, 2006.

(51) Int. Cl.
*G06K 9/00* (2006.01)
*G01N 21/00* (2006.01)
(52) U.S. Cl. ......... 382/110; 356/337; 356/432; 356/604
(58) Field of Classification Search .................. 382/110; 356/603, 604, 610, 301, 337, 947, 432
See application file for complete search history.

(56) References Cited

U.S. PATENT DOCUMENTS 6,958,815 B2    10/2005    Bevilacqua et al.
2007/0208510 A1    9/2007    Anderson et al.

OTHER PUBLICATIONS

Anderson e al. "Spatial-Frequency-Domain Imaging for Quality Assessment of Apples." Conference on Lasers and Electro-Optics, 2006 Quantum Electronics and Laser Science Conference, May 21, 2006, 2 pages.*
Cuccia et al. "Modulated Imaging: Quantitative Analysis and Tomography of Turbid Media in the Spatial-Frequency Domain." Optics Letters, vol. 30, No. 11, Jun. 1, 2005, pp. 1354-1356.*

* cited by examiner

*Primary Examiner* — Jon Chang
(74) *Attorney, Agent, or Firm* — Marcus C. Dawes; Daniel L. Dawes

(57) ABSTRACT

A method and an apparatus for noninvasively and quantitatively determining spatially resolved absorption and reduced scattering coefficients over a wide field-of-view of a food object, including fruit or produce, uses spatial-frequency-domain imaging (SFDI). A single modulated imaging platform is employed. It includes a broadband light source, a digital micromirror optically coupled to the light source to control a modulated light pattern directed onto the food object at a plurality of selected spatial frequencies, a multispectral camera for taking a spectral image of a reflected modulated light pattern from the food object, a spectrally variable filter optically coupled between the food object and the multispectral camera to select a discrete number of wavelengths for image capture, and a computer coupled to the digital micromirror, camera and variable filter to enable acquisition of the reflected modulated light pattern at the selected spatial frequencies.

22 Claims, 28 Drawing Sheets

Fig. 4a
Fig. 4c
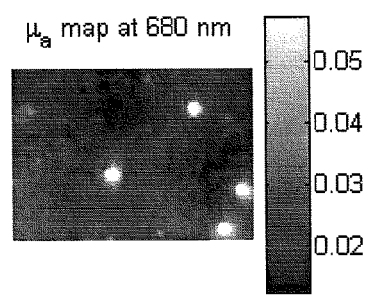
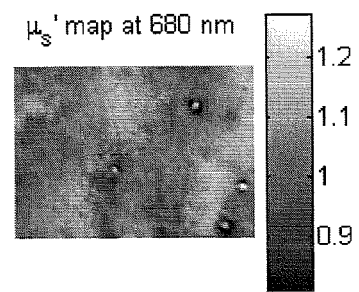
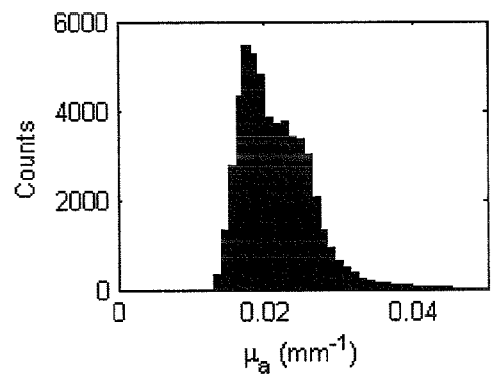
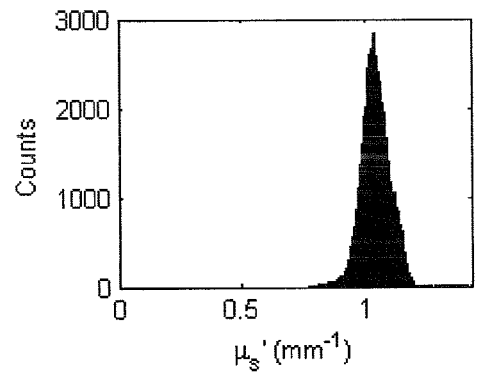
Fig. 4b
Fig. 4d

Fig. 5a
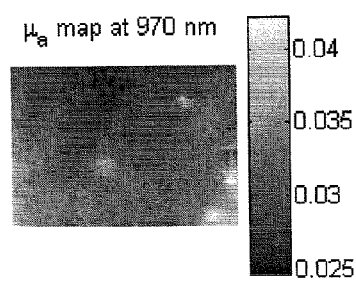
Fig. 5c
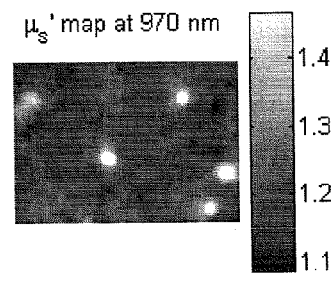
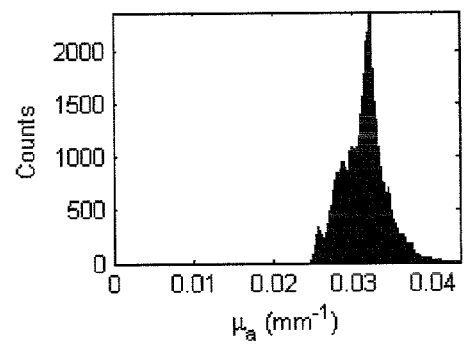
Fig. 5b
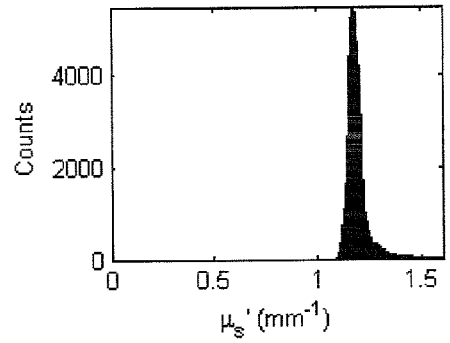
Fig. 5d

METHOD AND APPARATUS FOR PERFORMING QUALITATIVE AND QUANTITATIVE ANALYSIS OF PRODUCE (FRUIT, VEGETABLES) USING SPATIALLY STRUCTURED ILLUMINATION

RELATED APPLICATIONS

The present application is related to U.S. Provisional Patent Application Ser. No. 60/855,526, filed on Oct. 30, 2006, which is incorporated herein by reference and to which priority is claimed pursuant to 35 USC 119.

GOVERNMENT RIGHTS

This invention was made with Government Support under Grant No. RR001192, awarded by the National Institutes of Health. The Government has certain rights in this invention.

BACKGROUND OF THE INVENTION

1. Field of the Invention

The invention relates to the field of grading, characterizing or processing food, fruit or produce using optical methods and apparatus.

2. Description of the Prior Art

In U.S. Pat. No. 6,958,815 we disclosed a wide field, broadband, spatially modulated illumination of turbid media, incorporated herein by reference. This approach has potential for simultaneous surface and sub-surface mapping of media structure, function and composition. This method can be applied with no contact to the medium over a large area, and could be used in a variety of applications that require wide-field image characterization. The method was refined in U.S. patent application Ser. No. 11/336,065, incorporated herein by reference, directed to an improvement in a method for quantitative modulated imaging to perform depth sectioned reflectance or transmission imaging in a turbid medium, including the steps of encoding periodic pattern of illumination preferably with a fluorescent excitation wavelength when exposing a turbid medium to the periodic pattern to provide depth-resolved discrimination of structures within the turbid medium; and reconstructing a non-contact three dimensional image of the structure within a turbid medium.

Quality assurance is one of the most important goals in any field especially in the biomedical and agricultural field. Biomedical and agricultural technologies have many things in common since plant tissue has many similar components to animal tissue. In the biomedical and agricultural fields, quality assurance involves inspection, detection, and sorting. In the fruit industry, damage and defects reduce the market value of fruits and can cause significant economic loss. One defect having considerable negative impact in the fruit industry is bruising, particularly in the apple industry. In the worldwide fruit and vegetable industries, the reduction of bruising can provide the annual payback in the billions of dollars. The bruise is a consequence of a physical and/or chemical change, which can alter the color, flavor, and texture of the fruit and may be a result of external forces that occur during harvest, transportation, or handling. The detection of bruising in apples is a difficult task because the skin often obscures the appearance of underlying damage. In addition, the detection sensitivity is dependent on apple variety, time of bruise, harvest conditions, bruise type and severity.

Manual inspection of bruises is expensive, slow, and prone to error and inconsistency. Automated machine vision systems are needed to improve the inspection process. Machine vision systems are available for performing rapid, non-destructive quick scanning of the entire surface area of the fruit. These systems are being used for sorting by size, shape, and color; but defect detection such as bruise detection remains a challenge.

A limitation of these systems is that they typically operate in simple reflectance geometry and do not quantitatively distinguish between scattering and absorption effects. Structural and chemical information, while present in the recorded signals, is typically not provided in a detailed sense. Light penetration in multiple scattering media such as fruit, both scattering and absorption contribute to the distance-dependent attenuation. Light absorption is related to chemical components in fruit, including chlorophyll, sugar, and water. On the other hand, scattering is related to the physical structure of fruit, such as cell structure. Therefore, changes in scattering should correlate with changes in physical properties of fruit such as bruising. Machine vision systems that are able to distinguish absorption and scattering in a single measurement have the potential to provide an improved quantitative assessment of fruit. A number of single point near-infrared (NIR) systems have been developed to separate absorption and scattering in turbid biological materials, which can be classified as time-domain, frequency-domain, and steady-state spatial domain. In addition, some single point spectroscopic NIR measurements have been carried out in the time domain that enables separation and quantification of optical properties of fruit. However, single point techniques are generally limited in their ability to characterize volume spatial variability of fruit, and non-optical measurements on some fruits have demonstrated variation in properties such as sugar and acid content from one side to the other side. In addition, single point measurements are limited in characterizing spatial variable surface defects and contaminations such as bruises, side rots, flyspecks, molds, and fungal diseases on apples. Machine vision systems that can separate absorption and scattering over a large area of the fruit with a single measurement will enable a more comprehensive assessment of the condition of the fruit.

Spatial Frequency Domain Imaging (SFDI) is a non-contact optical imaging technology under development for various biomedical applications including skin cancer, and port wine stain characterization, and brain imaging. Compared to other imaging approaches, SFDI has the unique capability of enabling rapid, wide-field quantitative mapping of optical properties within a single measurement platform. While compatible with time-modulation methods, SFDI uses spatially-modulated illumination for imaging of turbid sample constituents. Spatially resolved absorption and scattering coefficients are subsequently deduced using an appropriate model of light propagation. Golden Delicious apples are particularly vulnerable to bruising.

BRIEF SUMMARY OF THE INVENTION

The illustrated embodiment of the invention is an improvement in an imaging method of using spatial-frequency-domain imaging (SFDI) for use in food processing comprising the step of noninvasively and quantitatively determining spatially resolved absorption and reduced scattering coefficients over a wide field-of-view of a food object, including fruit or produce.

The method further comprises the step of identifying surface characteristics and/or depth sectioned imaging of subsurface characteristics of the food object.

The method further comprises the step of simultaneously imaging fluorophore spectral characteristics of the food object.

The method further comprises the step of separating average background optical properties from heterogeneity components from a single image of the food object.

The method further comprises the step of separating average background fluorescence from a target fluorescence feature using selection of spatial frequency of illumination from a single image of the food object.

The method further comprises the step of separating a superficial fluorescent feature from a deep fluorescent feature based on selection of spatial frequency of illumination from a single image of the food object.

The method further comprises the step of assessing depth sensitivity as a function of source spatial frequency, wavelength selection and/or amplitude modulation to provide subsurface imaging/tomography.

The method further comprises the step of quantitative fluorescence imaging to deconvolve the effects of scattering and absorption from fluorophore spectra.

The method further comprises the step of performing both diffuse optical tomography and rapid, wide-field quantitative mapping of optical properties within a single measurement platform.

The method further comprises the step of determining therefrom pulp firmness, sugar content, bruise sensitivity, or fecal contamination of the food object.

The method further comprises the step of quantitatively determining spatially resolved absorption and reduced scattering coefficients over a wide field-of-view of a food object further comprises quantitatively determining severity of bruising in the food object by quantitative assessment of the mean scattering coefficient of a bruised region.

The illustrated embodiment of the invention is also an apparatus for noninvasively and quantitatively determining spatially resolved absorption and reduced scattering coefficients over a wide field-of-view of a food object, including fruit or produce, using spatial-frequency-domain imaging (SFDI) comprising a single modulated imaging platform comprising a broadband light source, a digital micromirror optically coupled to the light source to control a modulated light pattern directed onto the food object at a plurality of selected spatial frequencies, a multispectral camera for taking a spectral image of a reflected modulated light pattern from the food object, a spectrally variable filter optically coupled between the food object and the multispectral camera to select a discrete number of wavelengths for image capture, and a computer coupled to the digital micromirror, camera and variable filter to enable acquisition of the reflected modulated light pattern at the selected spatial frequencies.

The computer is arranged and configured and also controls the digital micromirror, camera and variable filter to perform any one of the above improved methods.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 4a is a quantitative absorption map and FIG. 4c is a quantitative scattering image map ($mm^{-1}$) for Golden Delicious apple with skin at 680 nm.

FIG. 4b is a pixel histogram corresponding to FIG. 4a and FIG. 4d is a pixel histogram corresponding to FIG. 4c.

FIGS. 5a and 5c are quantitative absorption and scattering image maps ($mm^{-1}$, top) for Golden Delicious apple with skin at 970 nm and FIGS. 5b and 5d are the corresponding pixel histograms.

FIG. 10a is a reflectance image at 680 nm with the ROI (dotted rectangle). FIG. 10b are quantitative absorption and scattering image maps ($mm^{-1}$, top) at 680 nm and corresponding pixel histograms (bottom). FIG. 10c are quantitative absorption and scattering image maps (mm–1, top) at 800 nm and corresponding pixel histograms (bottom). FIG. 10d are quantitative absorption and scattering image maps (mm–1, top) at 970 nm and corresponding pixel histograms (bottom). The bright white dots in the image maps are from the apple lenticels.

FIG. 11a is a reflectance image at 680 nm with the bruised ROI (dotted rectangle). FIG. 11b is a reflectance image at 680 nm with the non-bruised ROI (dotted rectangle). FIG. 11c is a graph showing the average absorption coefficients verses spectral wavelength for non-bruised region (open squares) and bruised region (open circles). FIG. 11d is a graph showing the average scattering coefficients versus spectral wavelength for non-bruised region (open squares) and bruised region (open circles).

FIG. 13a is a reflectance image at 680 nm with the ROI (dotted rectangle). FIG. 13b are quantitative absorption and scattering image maps (mm−1, top) at 680 nm and corresponding pixel histograms (bottom). FIG. 13c are quantitative absorption and scattering image maps (mm−1, top) at 800 nm and corresponding pixel histograms (bottom). FIG. 13d is are quantitative absorption and scattering image maps (mm−1, top) at 970 nm and corresponding pixel histograms (bottom). The bright white dots in the image maps are from the apple lenticels.

FIG. 14a is a reflectance image at 680 nm with the bruised ROI (dotted rectangle). FIG. 14b is a reflectance image at 680 nm with the non-bruised ROI (dotted rectangle). FIG. 14c is a graph of the average absorption coefficients verses spectral wavelength for non-bruised region (open squares) and bruised region (open circles). FIG. 14d is a graph of the average scattering coefficients verses spectral wavelength for non-bruised region (open squares) and bruised region (open circles).

Figure 1:
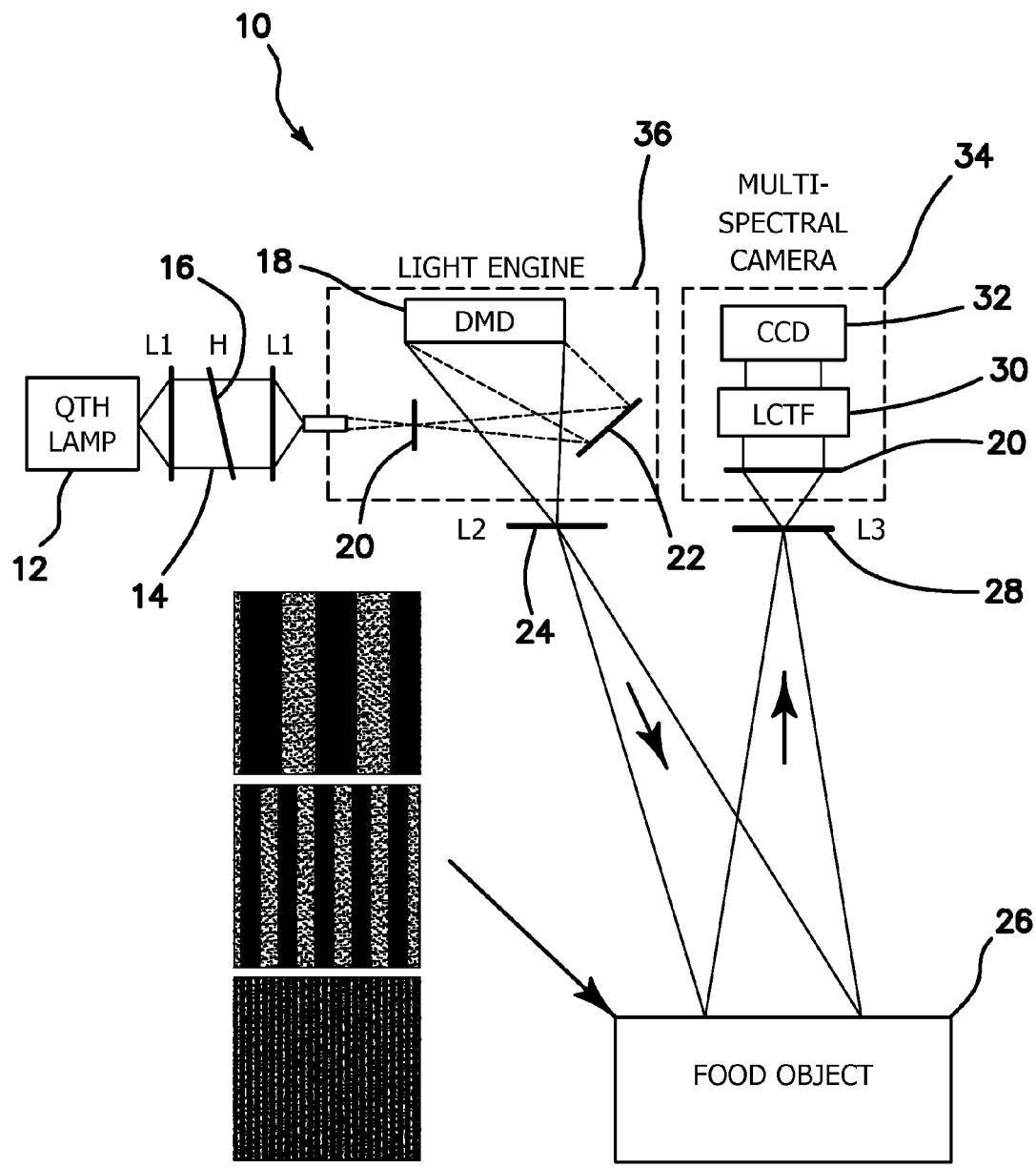
FIG. 1 is a schematic block diagram of the apparatus of the illustrated embodiment used to make the measurements of the claimed methodology.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

An imaging technique developed at the Beckman Laser Institute (BLI) for applications in the medical field, which has potential applications in the fruit industry, and is called spatial-frequency-domain imaging (SFDI; also known as Modulated Imaging). This technology is particularly compelling because it enables rapid quantitative determination of spatially resolved absorption and reduced scattering coefficients over a wide field-of-view. In addition, it has the potential to enable depth sectioned imaging, which may have utility in the identification of subsurface defects.

NIR instruments that are able to distinguish absorption and scattering in a single measurement have the potential to give a more accurate and complete picture of fruit. In addition, modulated imaging system can also provide surface or subsurface optical properties over an area of the fruit with a single measurement thus providing an even better quantitative picture of the condition of the fruit. Since fruit ripens from the inside out, during the maturation process there is a gradient in properties such as sugar content. Even mature fruit has natural variation in properties such as sugar and acid content from one side to another.

In addition to wide field imaging, the disclosed approach can provide:
a. Subsurface imaging/tomography: depth sensitivity to be assessed as a function of source spatial frequency, wavelength selection and/or amplitude modulation;
b. Optical properties determination over large surface;
c. Quantitative fluorescence imaging: For typical biological samples, measurement of quantitative fluorescence is confounded by the effects of scattering and absorption. The method disclosed here can provide both spatially resolved scattering and absorption properties in addition to fluorescence data. Hence, with the appropriate model of light propagation, one can deconvolve the effects of scattering and absorption from fluorophore spectra.
d. Separation of the average background optical properties from the heterogeneity components from a single image;
e. Separation of background fluorescence from target fluorescence based on selection of spatial frequency of illumination; and
f. Separation of superficial fluorescent features from deep fluorescent features based on selection of spatial frequency of illumination.

Spatial-Frequency-Domain Imaging (SFDI) is applied for the first time by the present invention to separate and quantify broadband spatially-resolved optical properties of fruit. Spatial frequency domain imaging (SFDI) is a novel non-contact optical imaging technology under development for various medical applications including fluorescence tomography, skin cancer characterization and local tissue oximetry of wounds. Compared to other imaging approaches, SFDI has the unique capability of performing rapid, wide-field quantitative mapping of optical properties within a single measurement platform. While compatible with time-modulation methods, SFDI alternatively uses spatially-modulated illumination for imaging of turbid sample constituents.

Compared to other imaging approaches, SFDI has the unique capability of performing both diffuse optical tomography and rapid, wide-field quantitative mapping of optical properties within a single measurement platform. While compatible with time-modulation methods, SFDI alternatively uses spatially-modulated illumination for imaging of tissue constituents. Periodic illumination patterns of various spatial frequencies are projected over a large area of a sample. The reflected image is modified from the illumination pattern due to the turbidity of the sample. Typically, sine-wave illumination patterns are used. The demodulation of these spatially-modulated waves characterizes the modulation transfer function (MTF) of the material, and embodies the sample structural and optical property information.

The spatial-frequency dependence of sample reflectance encodes both depth and optical property information. Introducing a spatially-modulated source, Eq (2), into the steady-state diffusion equation, Eq (1):

$$\nabla^2 \phi - k^2 \phi = S \quad (1)$$

$$S = S_0[1 + M\sin(2\pi f_x x)] \quad (2)$$

where $$k = \sqrt{3\mu_a(\mu_a + \mu'_s)} = \mu_{eff} \quad (3)$$

and where $1/\mu_{eff}$ is the effective penetration depth of the illumination, gives results:

$$\partial_z^2 \phi_{AC} - (k^2 + (2\pi f_x)^2)\phi_{AC} = S_0 \quad (4)$$

$$\mu'^2_{eff} = 3\mu_a(\mu_a + \mu'_s) + (2\pi f_x)^2 \quad (5)$$

Here, $\Phi$ is the internal fluence, S the illumination source, M the modulation depth of the illumination, and $f_x$ the spatial frequency of illumination, and $\Phi_{AC}$ refers to the harmonically varying component of the fluence. The spatially-modulated wave propagates in turbid media as that from planar illumination source $S_0$ would, except that the penetration depth, $1/\mu'_{\mathit{eff}}$, depends on the spatial frequency of illumination.

There are two major implications to Equations 4 and 5. First, varying the spatial frequency of the illumination pattern allows one to control the depth sensitivity of detection inside the turbid medium, illustrated in FIG. 2a. Second, by analyzing the frequency-dependent reflectance, one can quantitatively sample the optical properties of the medium.

Simulated frequency responses for varying optical properties demonstrate the potential for determination of optical properties. This is analogous to the frequency-domain photon migration (FDPM) technique, a variant of diffuse optical spectroscopy, where the temporal frequency of the photon density waves is related to the spatial frequency through the speed of photon density wave propagation in the medium of interest.

In practice, the illumination is in the form $\cos(2\pi f_x x + \phi) + \frac{1}{2}$, containing a DC component to allow for modulation from 0 to 1. In order to view the reflectance due to the AC and DC components separately, a standard technique in signal processing is employed. This requires illuminating the sample three times at the same spatial frequency, with phase offsets of 0, 120 and 240 degrees. An image of the AC modulated reflectance can be calculated using Eq (5), $$AC = \frac{\sqrt{3}}{2}\sqrt{(A-B)^2 + (B-C)^2 + (C-A)^2} \quad (5)$$

where A, B, and C represent the reflectance images with shifted spatial phases. This has been recently employed for use in confocal microscopy.

The specular reflection is carefully avoided by illuminating at a small angle to the normal direction, and by using crossed linear polarizers. Interference filters allow for narrow wavelength band selection. A spectral or reflectance standard is used to calibrate the measured intensity, and to correct for spatial non uniformity in both the illumination and imaging systems.

The initial data demonstrates that modulated imaging can simultaneously accommodate the measurement of the optical properties over a wide field-of-view in addition to a fast and economical procedure to achieve depth sectioning in turbid media. In principle this can be carried out using a simple data acquisition geometry and has the potential to be both fast and inexpensive. With the addition of appropriate excitation filters, the capability of fluorescence imaging can easily be incorporated into the instrument. Because SFDI can be used to quantitatively deduce absorption and reduced scattering coefficients in a spatially resolved manner, we have the capability of correcting measured fluorescence images for the effects of these parameters. Hence SFDI, when combined with fluorescence imaging and an appropriate model of light propagation, can be used to accurately quantify the concentrations of the fluorophores contributing to the measured fluorescence emission.

A diagram of the system of the illustrated embodiment is shown in FIG. 1. A modulated imaging platform 10 is comprised of a quartz tungsten halogen lamp (QTH) 12 or other light source which is projected into an aspheric condenser 14 which includes a hybrid hot mirror 16. The beam of the halogen lamp 10 is expanded to match the digital micromirror device (DMD) 18. The light is focused through a polarizer 20 onto a mirror 22 and matched to a digital micromirror device 18, which are combined to provide a light engine 36. The DMD 18, 1024×768 binary mirrors, based on the DLP™ technology developed by Texas Instruments, is used to control the light pattern projected on the object 26. An image is then projected from the digital micromirror device 18 through a projection lens 24 onto the object of interest 26. A multispectral camera 34 with a camera lens 28 is focused on the object 26, whose image is filtered by a liquid crystal tunable filter 30 onto a CCD imaging array 32. Each pixel acts similarly to an avalanche photodiode, allowing simultaneously very high sensitivity and dynamic range at fast readout rates (up to 10 MHz). Filter wheel 30 is used to select a discrete number of wavelengths. Linear polarizers 20 are introduced into the source and detection light paths to measure both parallel and perpendicular polarization. The DMD 18, CCD 32 and filter wheel 30 are synchronized by a computer (not shown), enabling fast acquisition of a series of patterns with various spatial frequencies.

Periodic illumination patterns of various spatial frequencies, as shown to the bottom left in FIG. 1 are projected over a large area of the sample or object 26 (5 mm-10 cm), and without the need for physical contact to the fruit, produce or object 26. The reflected image from object 26 recorded in camera 34 is modified from the illumination pattern due to the turbidity of the sample. The demodulation of these spatially-modulated waves characterizes the modulation transfer function (MTF) of the material of object 26, and embodies the object's structural and optical property information. Varying the spatial frequency of the illumination pattern allows one to control the depth sensitivity of detection inside the turbid medium comprising object 26. In addition, by analyzing the frequency-dependent reflectance, one can quantitatively sample the optical properties of the medium of object 26.

A full description of SFDI data processing has been published in Cuccia et. al., *Modulated imaging: quantitative analysis and tomography of turbid media in the spatial-frequency domain*. Optics Letters, 2005. 30 (11): p. 1354-1356. In summary, the diffuse reflectance, $R_d$, versus spatial frequency, $f_x = k/2\pi$, can be written as:

$$R_d(k) = \frac{3A\mu'_s/\mu_{tr}}{(\mu'_{\mathit{eff}}/\mu_{tr} + 1)(\mu'_{\mathit{eff}}/\mu_{tr} + 3A)} \quad (6)$$

where $\mu_{tr} = \mu_a + \mu_s'$ is the transport coefficient, $\mu_{\mathit{eff}}' = [3\mu_a^2 + k^2]^{1/2}$, $\mu_{\mathit{eff}} = [3\mu_a \mu_{tr}]^{1/2}$, $\mu_a$ is the absorption coefficient, $\mu_s' = \mu_s(1-g)$ is the reduced scattering coefficient, g is the cosine of the average scattering angle, and A is a proportionality constant. On a pixel-by-pixel basis, measurements of diffuse reflectance at each spatial frequency are calculated by calibrated measurement and demodulation of three spatial phase projections. Diffuse reflectance versus spatial frequency is then non-linearly fit to Equation 6 to extract the local absorption and reduced scattering properties. This process is repeated for each wavelength, resulting in multi-spectral absorption and scattering spectra at each pixel. In these measurements, we rely on the homogeneous reflectance model of Equation 1 to extract depth-averaged "projections" of absorption and reduced scattering over the penetration depth of the light.

The core SFDI platform was originally described by Cuccia above and later followed by a detailed description of spatial frequency domain measurement, calibration, and analysis. In order to extend the platform to multi-spectral sampling, the system as shown in FIG. 1 was arranged and configured to cover the spectral range from 650 to 1000 nm. A broadband NIR digital projector, comprising a 250 W quartz-tungsten-halogen lamp (Model 6334, Newport Corp.), a 1024×768 binary digital micromirror device (DMD), (0.7XGA 12° DDR DMD, Texas Instruments), commercial projector light engine optics, and a fixed focal length projection lens (f=100 mm) illuminates object 26 with grayscale sinusoid patterns over a 30×40 mm field of view. The diffusely reflected light is imaged using a CRI Nuance™ CCD camera system 34, incorporating a liquid crystal tunable filter (LCTF) 30 with a 10 nm bandwidth and a variable center wavelength between 650-1100 nm. For measurements of objects 26 with rough surfaces such as fruit, specular reflection is rejected using crossed linear polarizers in the illumination and detection portions of FIG. 1. A standard reflectance phantom with known optical properties was used to calibrate the measured intensity and to correct for spatial non-uniformity in both the illumination and imaging systems of FIG. 1. The optical properties of the phantom were previously determined using broadband frequency-domain photon migration.

SFDI measurements of several species and varieties of fruit (Golden Delicious apples, Gala apples, peaches, nectarines, and tomatoes) were acquired at 32 wavelengths between 650 and 980 nm, and over a 30×40 mm field of view. The fruit was obtained from local food stores, and at least five from each species and varieties were obtained. To compensate for the wavelength-dependent illumination and detection throughput, image integration time was chosen at each wavelength to fill the dynamic range of the 12-bit camera For example, the Golden Delicious apple integration times ranged from 55 ms (650 nm) to 1.4 s (980 nm). At each wavelength, diffuse reflectance maps were measured at ten equally-spaced spatial frequencies (from $f_x$=0 to 0.12 mm$^{-1}$), with three phases of patterns at each frequency (0, 120 and 240°). Ten frequency spatial frequencies (from $f_x$=0 to 0.12 mm$^{-1}$) were selected to accurately capture the modulation transfer function of the fruit measured. In total, the 960-image MI dataset was acquired in less than 6 minutes per imaged area. For each sample, measurements were performed on three positions around the fruit.

The time required to process the data depends on the size of the image, the number of wavelengths, and the pixel bin size. The analysis time for the fruits ranged from minutes for a small region-or-interest (ROI) (10×10 mm) with a bin size of five to hours for a very large ROI (30×40 mm) with a bin size of one.

Figure 2A:
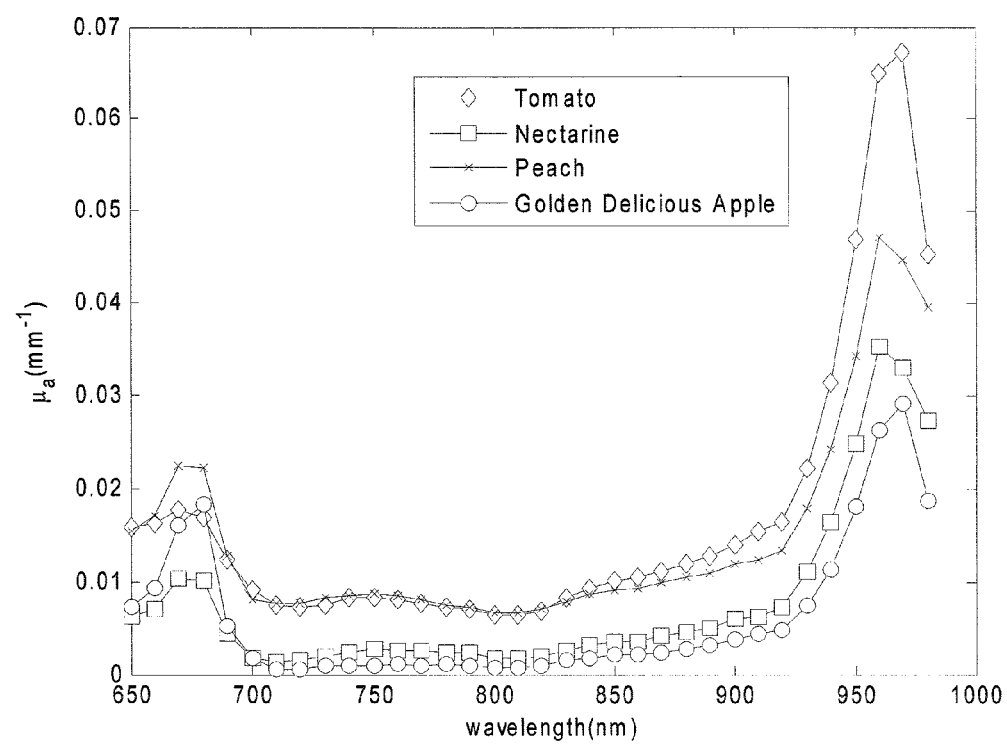
FIG. 2a is a graph of the average absorption coefficients verses spectral wavelength for tomato (open diamonds), nectarine (open squares), peach (crosses) and Golden Delicious apple (open circles).
Figure 2B:
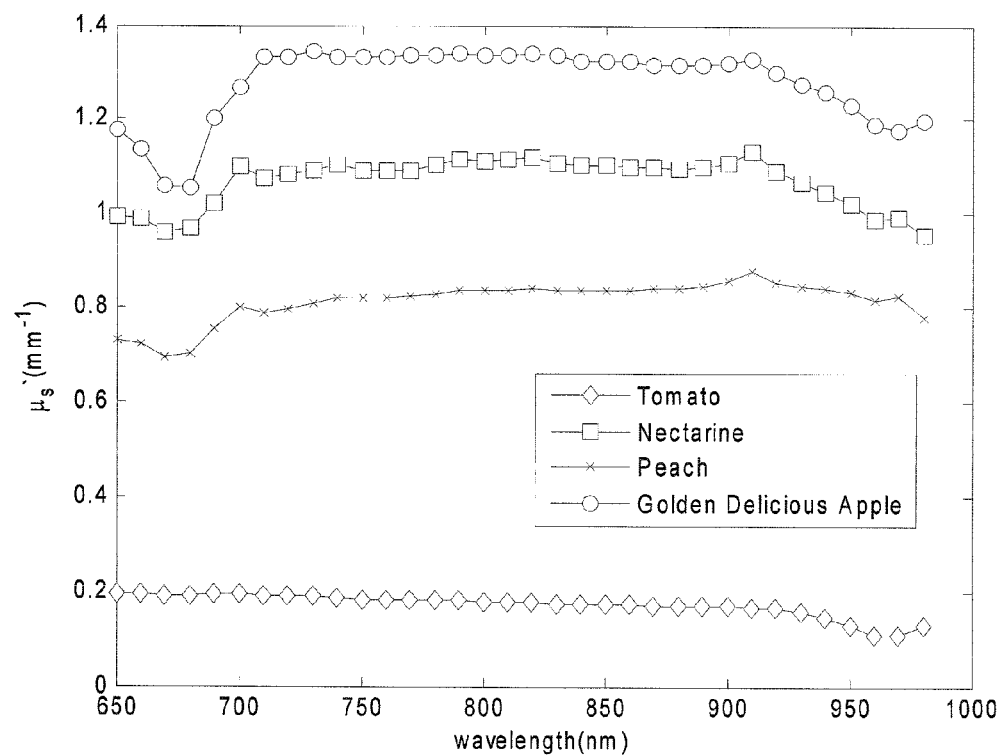
FIG. 2b is a graph of the average scattering coefficients verses spectral wavelength for tomato (open diamonds), nectarine (open squares), peach (crosses) and Golden Delicious apple (open circles).

Typical measured absorption spectra for tomato, nectarine, peach and Golden Delicious apple are shown in FIG. 2(a). For all fruits, the absorption is dominated by the water peak, centered near 970 nm. The second absorption maximum, centered around 675 nm is attributed to chlorophyll. Typical measured scattering spectra verses spectral wavelength for tomato, nectarine, peach and Golden Delicious apple are illustrated in FIG. 2(b). FIG. 2(b) shows a dip in the scattering coefficients near 675 nm for nectarine, peach and Golden Delicious apple. In addition, there is a slight decrease in scattering with increasing wavelength for the tomato and nectarine beyond 900 nm. We attributed these results to our present analytical model. The absorption and scattering coefficients were obtained from fitting the experimental data with a standard solution of the diffusion approximation to the radiative transport equation for a semi-infinite homogeneous medium.

Figure 3A:
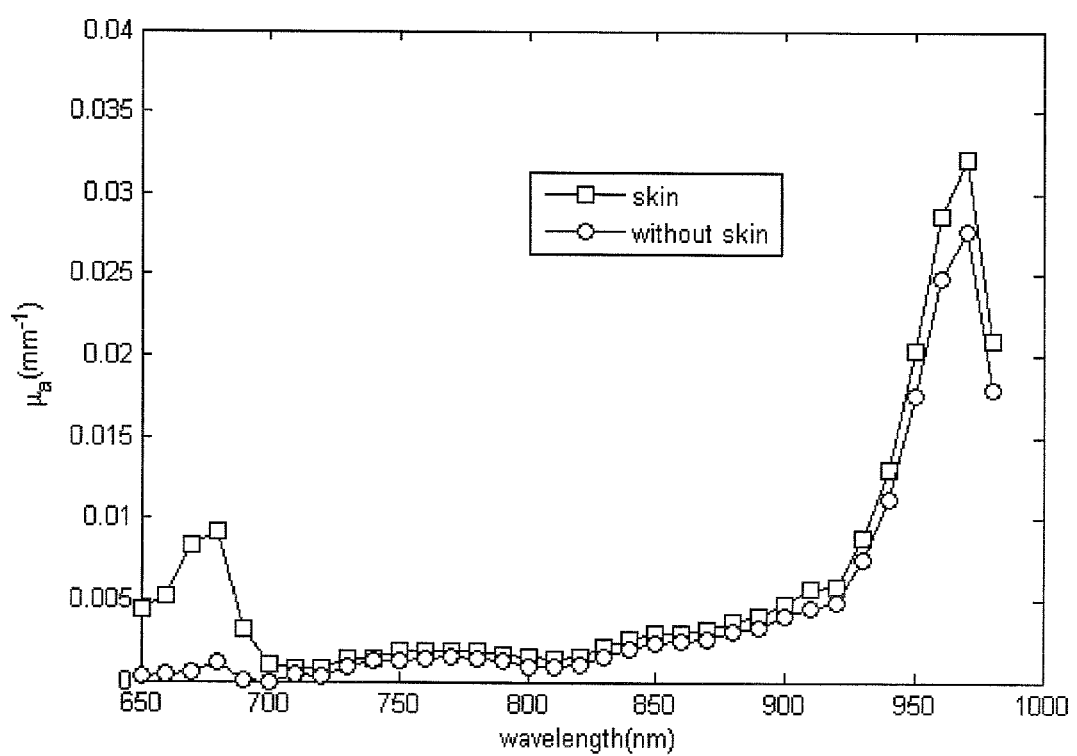
FIG. 3a is a graph of the average absorption coefficients verses spectral wavelength for a Golden Delicious apple with skin (open squares) and without skin (open circles).
Figure 3B:
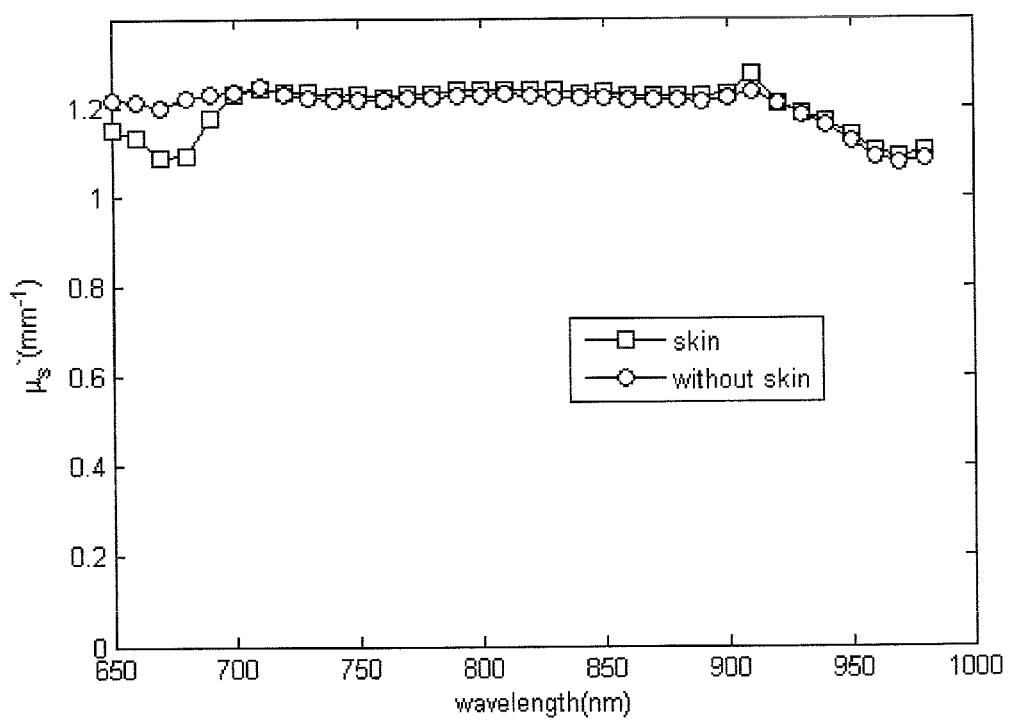
FIG. 3b is a graph of the average scattering coefficients verses spectral wavelength for a Golden Delicious apple with skin (open squares) and without skin (open circles).

From Mie theory for a semi-infinite homogeneous medium, the scattering coefficients should decrease with a power law dependence with increasing wavelength. On the other hand, apple fruit is a two layer medium consisting of an outer skin layer containing chlorophyll and an inner region consisting of pulp. To gain insight into the effect of the outer skin layer, measurements were performed on apple fruit with and without the skin layer. Typical absorption coefficients and scattering coefficients verses spectral wavelength for Golden Delicious apple with and without the outer skin are shown in FIGS. 3a and 3b respectively. When the outer skin surface is removed from the Golden Delicious apple, there is a large decrease in the absorption chlorophyll peak near 670 nm as shown in FIG. 3a. Removal of the skin also causes the scattering dip at the 670 nm to disappear as shown in FIG. 3b. These results indicate that fruit skin can have a substantial contribution to SFDI measurements.

FIGS. 4a-4c and 5a-5d illustrate the spatial information that can be accessed using SFDI for two (680 nm and 970 nm) of the 32 wavelength images obtained. The two figures contain a spatial map in FIGS. 4a, 4c, 5a, and 5c of the spatially resolved absorption and scattering properties for a Golden Delicious apple with the skin intact that were obtained by performing a frequency fit at each CCD pixel. To the right of each image is a vertical grey scale (mm$^{-1}$). As the magnitude of the absorption or scattering coefficient increases, the map shifts from black to grey and finally, white. FIGS. 4b, 4d, 5b and 5d are histograms obtained from all pixels within the total field-of-view. The vertical axis indicates the frequency of occurrence of the magnitude of the absorption or scattering coefficient (horizontal axis) determined at each pixel. The bright white dots in the images are from the Golden Delicious apple lenticels, which were observed visually with no instrumentation.

Figure 6:
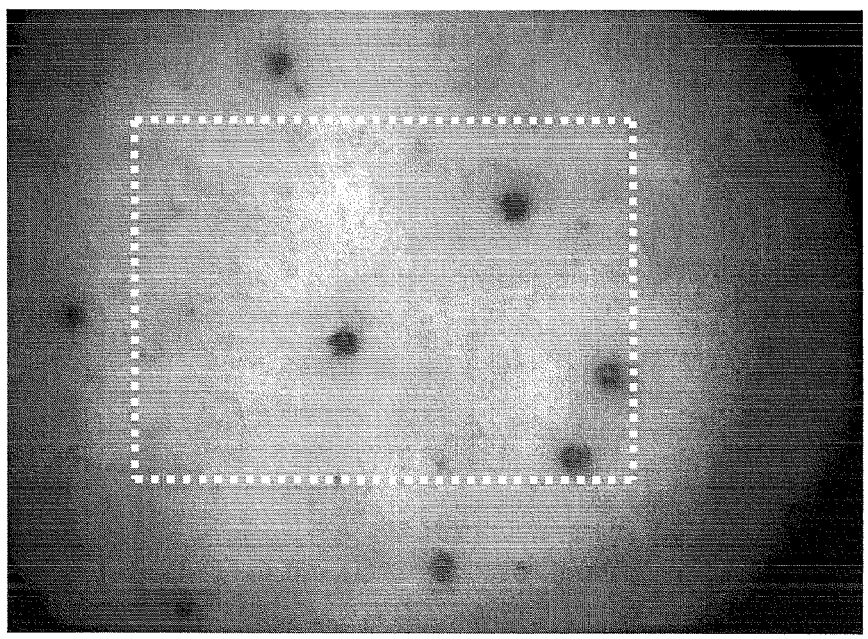
FIG. 6 is a Golden Delicious apple reflectance image with the range of interest (ROI) shown in the dotted rectangle.

For reference, FIG. 6 shows a reflectance image of the Golden Delicious apple with the range of interest ROI (dotted rectangle) before SFDI image analysis. These preliminary results show that fruit such as apples have large variation in optical properties across the fruit. To our knowledge this is the first report of wide-field imaging of quantitative optical properties in the spatial-frequency-domain for fruit.

A variety of apple samples, including Granny Smith, Gala, Red Delicious, and Fuji, were acquired from local supplies and growers (Bidart Brothers; Bakersfield, Calif.). The apples were selected to be free from blemishes and bruises. Each apple is placed on a sample holder with the stem end-calyx axis positioned horizontally. A location centered on the equator of the apple is selected for SFDI chlorophyll-fluorescence image acquisition. At each location, the wavelength of the illumination is swept using a combination of filter wheel and liquid crystal tunable filter 30 to obtain multiple wavelength spectral and chlorophyll fluorescence images. For each wavelength band, the spatial frequency of the illumination is swept as discussed in the previous section. The apple is then rotated a quarter turn and the measurements repeated until all four locations were tested. This procedure for imaging apples is implicit to sugar and bruise measurements.

In another experiment Golden Delicious apples were free from blemishes and bruises. An apple bruising device was designed and constructed for the application of a measured and reproducible force to induce bruising on test apples. The device consisted of a 60 cm long clear plastic hollow tube with a 19 mm inside diameter mounted vertically on a platform. An apple was placed on a cushioned holder with the stem end-calyx axis positioned horizontally and directly below the tube. A 110 gram steel cylindrical weight with a softly-curved end was inserted in the tube at predetermined heights and released for impact on the apple position directly below. After bruising, the end of the tube contacting the apple was used as a guide for drawing a circle around the bruised area for later identification. Two different heights (5.6 and 29.2 cm) were used to produce low and high bruising, respectively. The impact energy was calculated from the weight and heights to be 0.06 and 0.315 Joules. After bruising, the apple samples were stored in a refrigerator at 5° C. for 25 hours for the bruises to develop. Apples were taken out of the refrigerator and left at room temperature (25° C.) for three hours prior to imaging.

SFDI measurements were made on Golden Delicious apples with high bruising (0.315 J), and low bruising (0.06 J). For each bruise region, measurements were made at 32 wavelengths between 650 and 980 nm, and over a 21×33 mm field of view. To compensate for the wavelength-dependent illumination and detection throughput, integration time was chosen at each wavelength to fill the dynamic range of the 12-bit camera. For the Golden Delicious apples used here, integration times ranged from 15 ms (650 nm) to 500 ms (980 nm). At each wavelength, diffuse reflectance maps were measured at nine equally-spaced spatial frequencies (from $f_x$=0.0149 to 0.1344 mm−1), with three phases of patterns at each frequency (0, 120 and 2500). Nine spatial frequencies (from $f_x$=0.0149 to 0.1344 mm−1), which were determined experimentally, were used to ensure that the modulation transfer function of the apples was measured accurately. In total, the 864-image dataset was acquired in less than 6 minutes per imaged area. The absorption and scattering coefficients were obtained by fitting the experimental data with a standard solution of the diffusion approximation to the radiative transport equation for a semi-infinite homogeneous medium. The data processing was carried out using a standard desktop computer (Intel Pentium D, 3.0 GHz, 2 GB RAM). The time required to process the data depends on the size of the image, the number of wavelengths, and the pixel bin size. Currently, the analysis time for apple data ranged from a few minutes for a small region-or-interest (ROI) (10×10 mm) with a pixel bin size of 5×5 pixels to 60 minutes for a very large ROI (21×33 mm) with a pixel bin size of one. Although the acquisition and analysis times were long, a rapid apple bruise imaging system could be constructed operating at video rates by using only two spatial frequencies and one or two wavelengths.

Figure 10A:
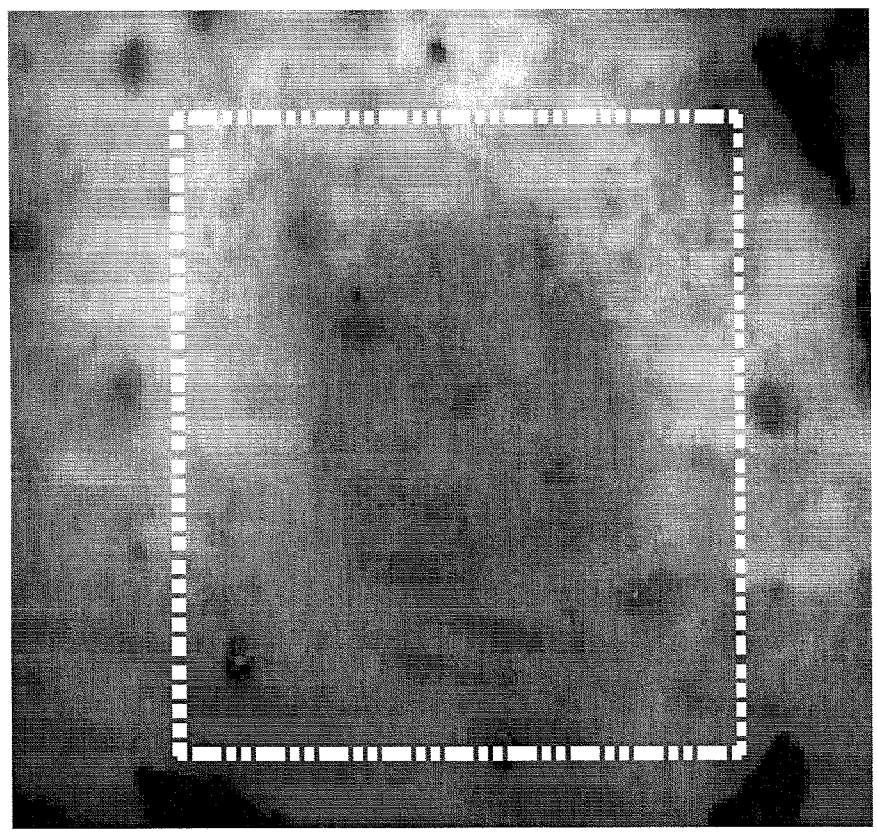
FIGS. 10a-10d are Golden Delicious apple SFDI spatial imaging results for 0.315 J level bruises.

FIGS. 10a-10d shows typical SFDI spatial maps for a bruised (0.315 J bruise level) region on a Golden Delicious apple for three (680 nm, 800 nm, and 970 nm) of the 32 wavelength images obtained. FIG. 10a shows a reflectance image (680 nm) with the range of interest ROI (dotted rectangle) before SFDI image analysis of the bruised and non-bruised region. The bruised region is visible within the ROI as a dark circular area. The dark spots are apple lenticels, which were observed visually without the aid of instrumentation. The bruise diameter, approximately 10 mm, was determined by measuring the diameter of the indentation caused by the impact. The depth of the bruise, approximately 5 mm, was determined by slicing out a cross section of the bruised region and measuring the distance of the discoloration from the surface.

Figure 10B:
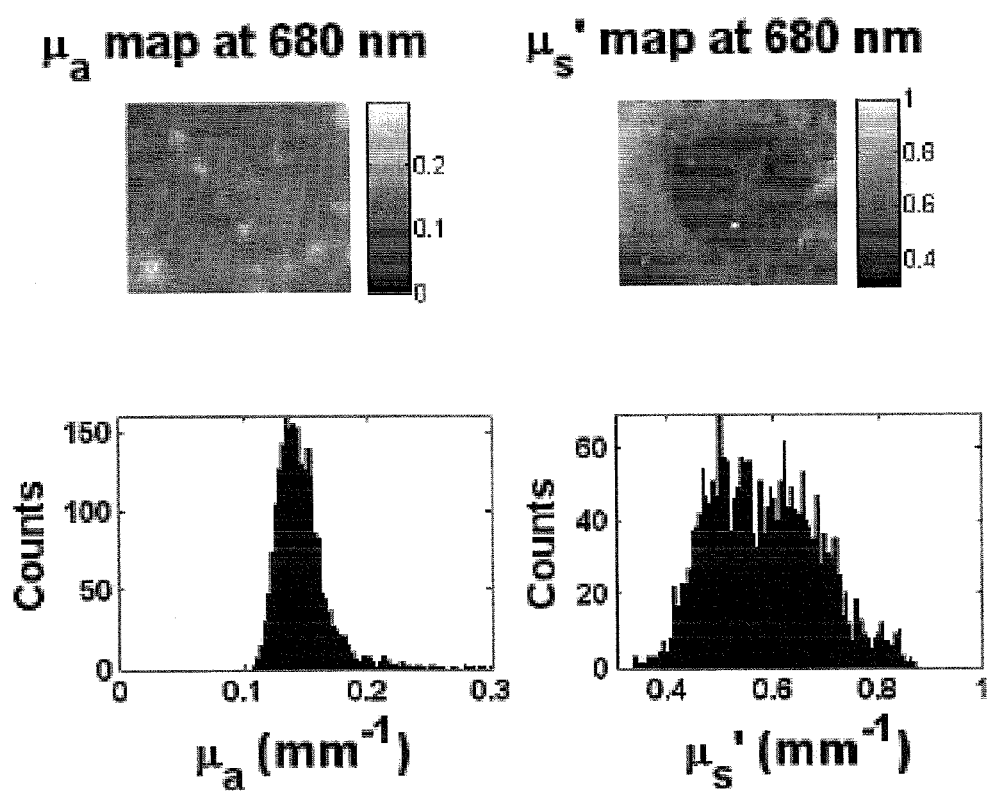
Figure 10C:
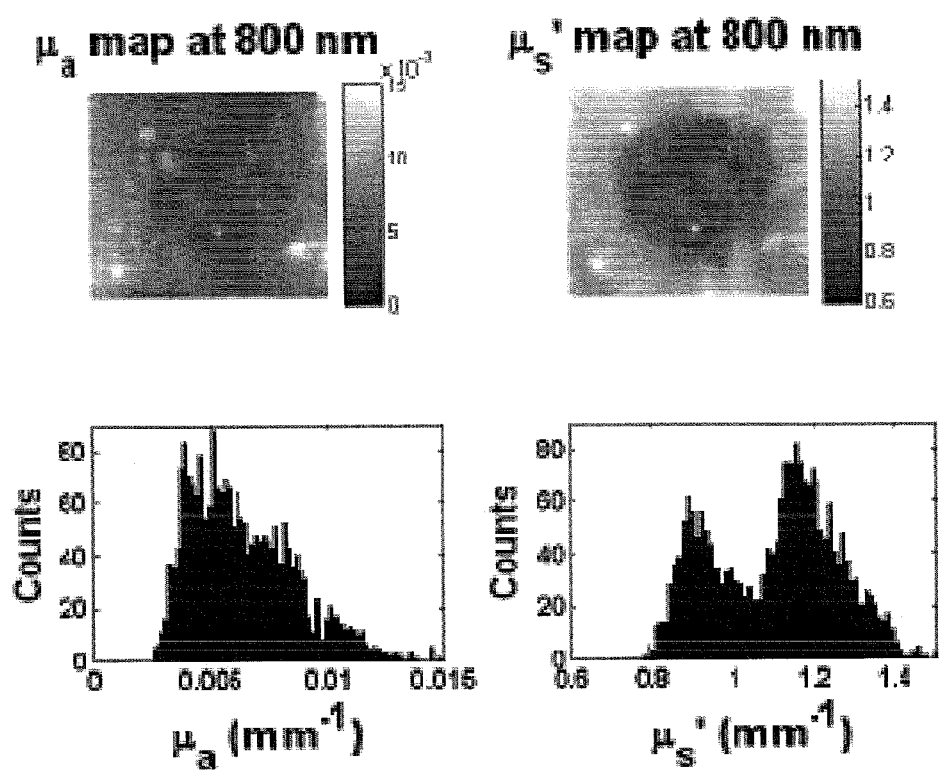
Figure 10D:
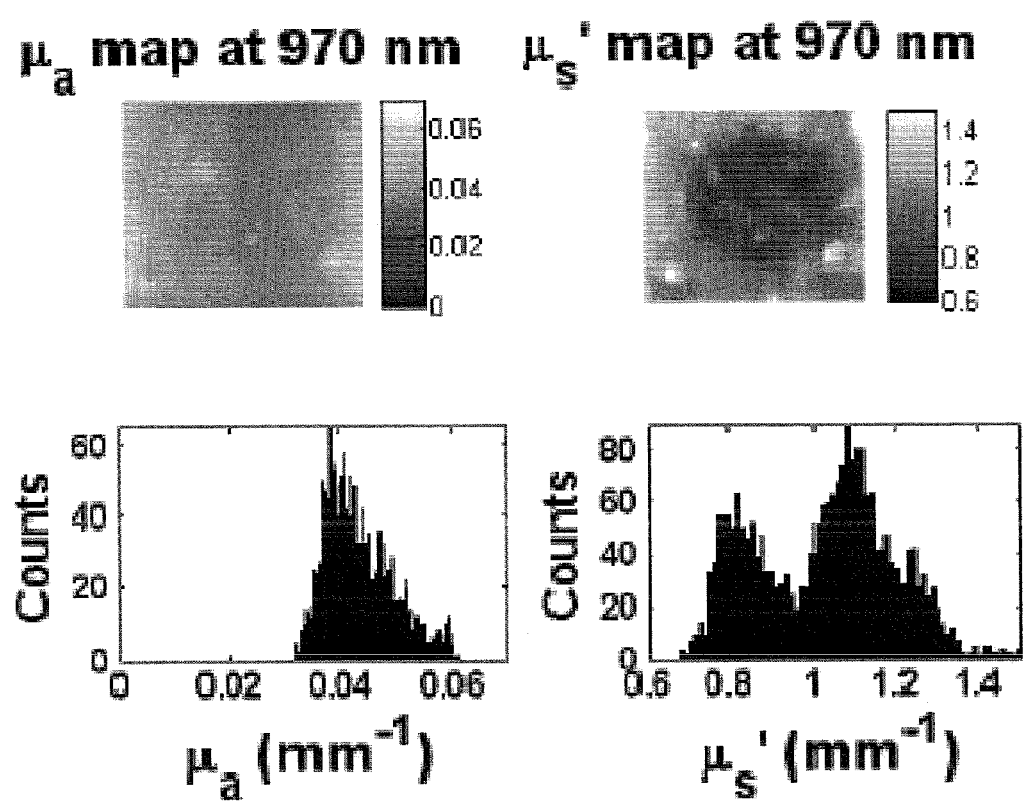

FIGS. 10b, 10c, and 10d contain spatial maps in the top figures of the spatially resolved absorption and scattering properties that were obtained by performing a frequency fit at each CCD pixel. To the right of each image is a vertical grey scale (mm−1). As the magnitude of the absorption or scattering coefficient increases, the map shifts from black to grey and finally, white. The bruise region is clearly visible in all three scattering images which is the top right figure in FIGS. 10b, 10c, and 10d. The circular bruised region has lower scattering coefficients than the non-bruised outer region. At the bottom of each spatial map is a histogram obtained from all pixels within the total ROI. The vertical axis indicates the frequency of occurrence of the magnitude of the absorption or scattering coefficient (horizontal axis) determined at each pixel. Two distributions are visible; one for the bruised region (lower scattering coefficients), and one for the non-bruised region (higher scattering coefficients). The bright white dots in the images are from the Golden Delicious apple lenticels. The lenticels have higher scattering coefficients because they are openings in the apple surface. These openings have a larger refraction index change than the cell structural matrix of the apple; thus they demonstrate small localized regions of high scattering.

Figure 11A:
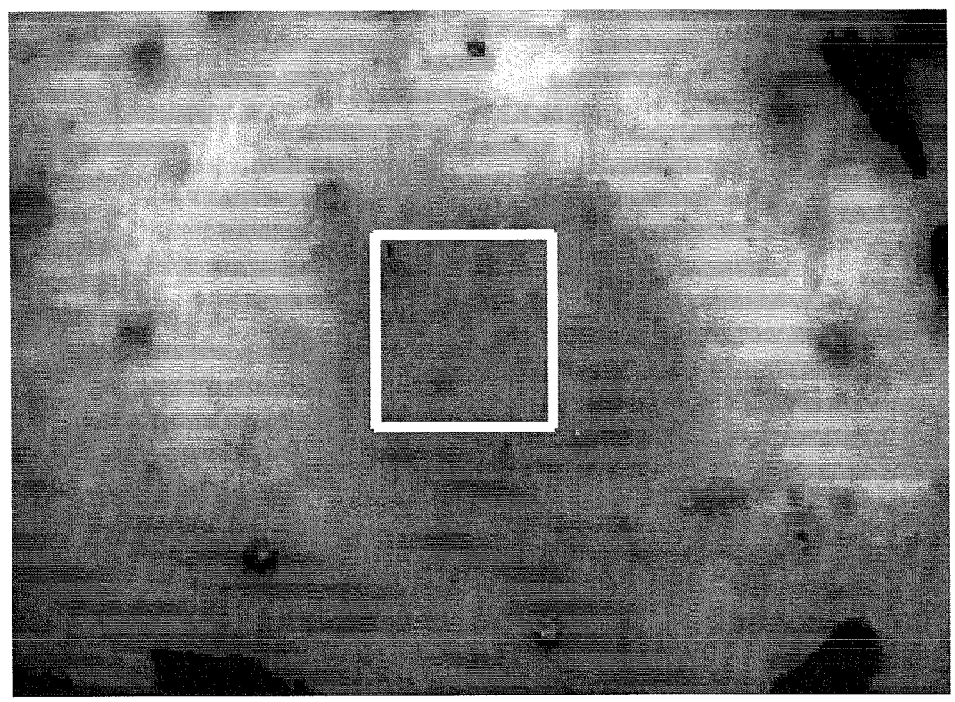
FIGS. 11a-11d show Golden Delicious apple SFDI average absorption and scattering spectra results for 0.315 J bruises.
Figure 11B:
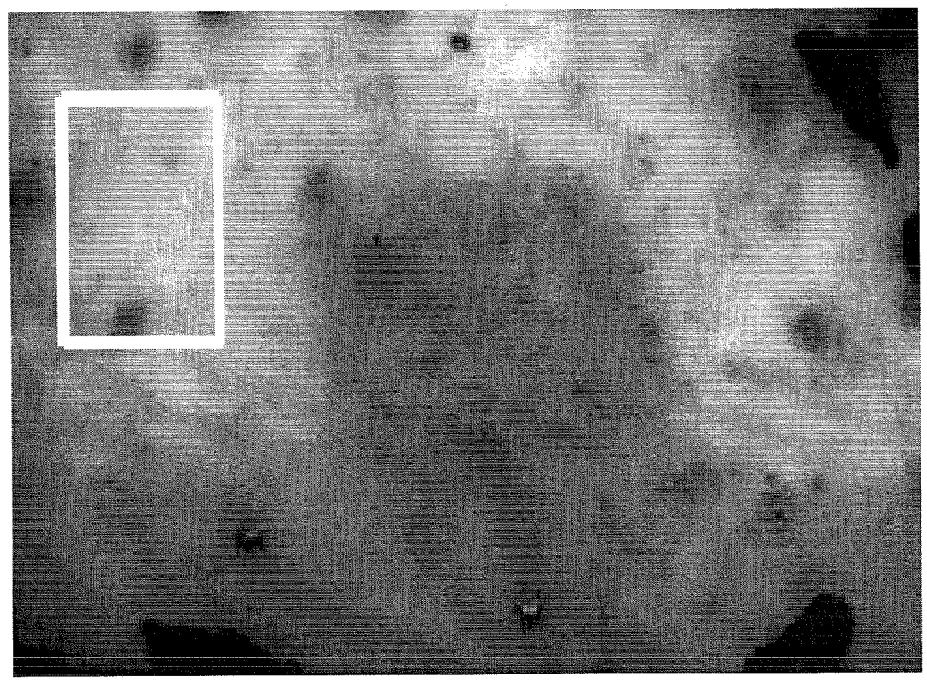
Figure 11C:
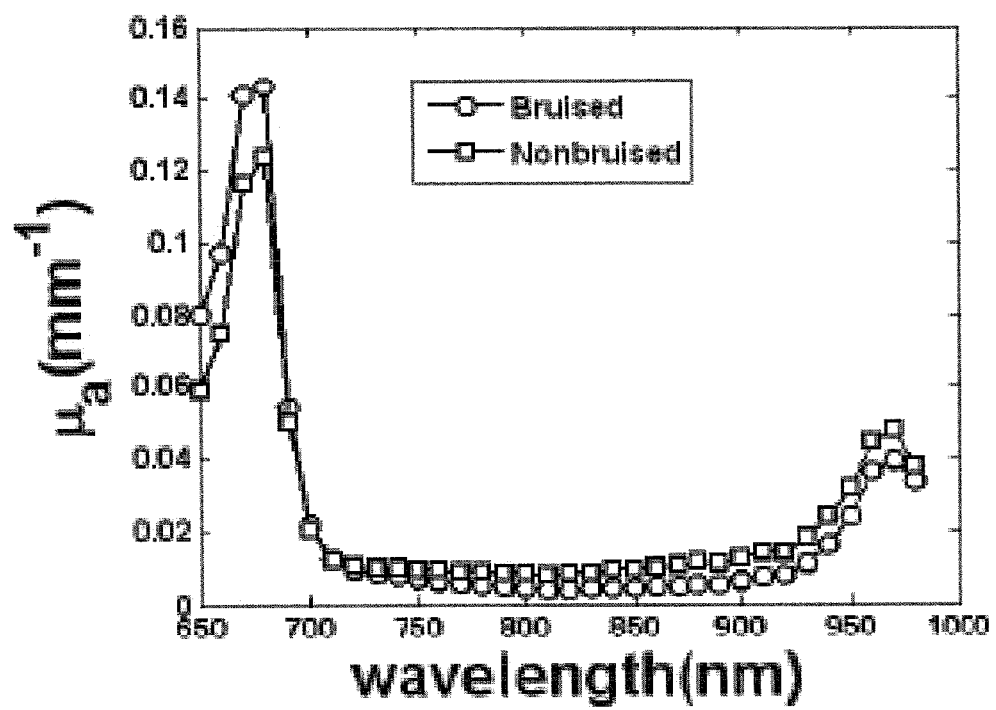

FIGS. 11a-11d show SFDI absorption and scattering spectra from 650 nm to 980 nm for a bruised (0.315 J bruise level) and non-bruised region on the same Golden Delicious apple as shown in FIGS. 10a-10d. FIG. 11a is a reflectance image at 680 nm with the bruised ROI (dotted rectangle), and FIG. 11b is a reflectance image at 680 nm with a near-by non-bruised ROI (dotted rectangle). Calculated absorption spectra for the bruised and non-bruised ROI are shown in FIG. 11c. The bruised and nonbruised plots are very similar, which is expected since bruising is primarily a structural change in the apple at these wavelengths. Both absorption spectra are dominated by two peaks; one centered near 970 nm from water and a second peak centered around 675 nm from chlorophyll a.

Figure 11D:
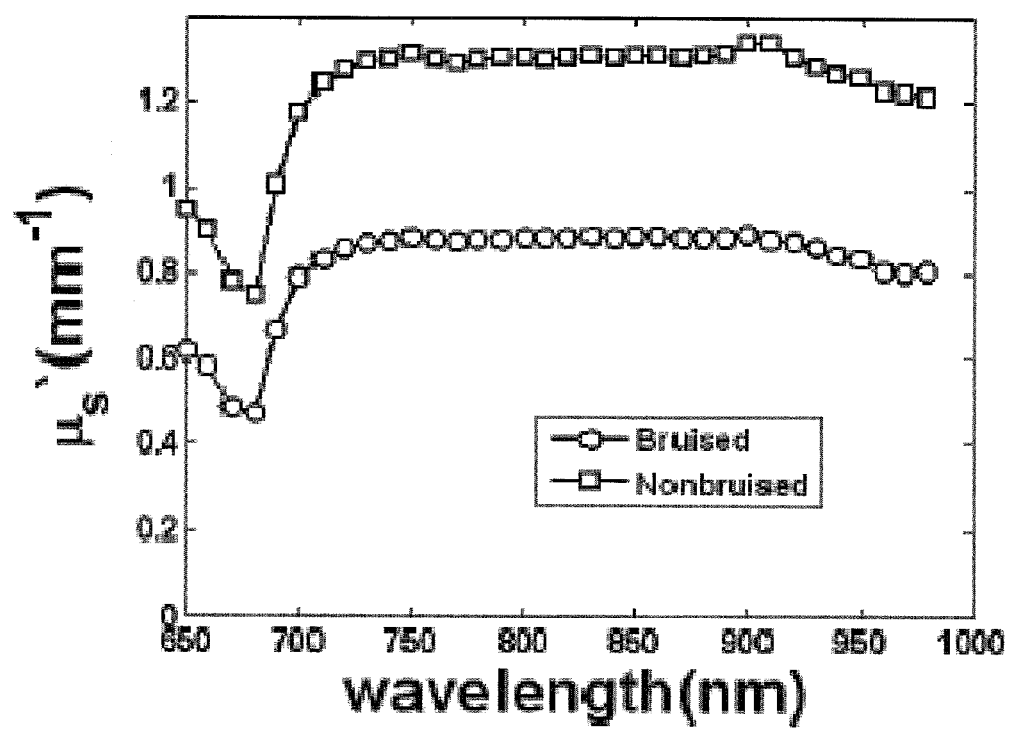

Calculated scattering spectra for the bruised and non-bruised ROI are shown in FIG. 11d. There is a large difference in the scattering coefficients between the bruised and non-bruised regions between 700 nm and 980 nm. For example, at 800 nm the non-bruised mean scattering coefficient is approximately 1.3 mm−1 with a standard deviation of 0.087, whereas the bruised mean scattering coefficient is approximately 0.88 mm−1 with a standard deviation of 0.057. FIG. 11d shows a large dip in the scattering coefficients near 675 nm for both the bruised and non-bruised regions. Mie theory predicts a monotonic decrease in scattering coefficient with increasing wavelength. We believe that this occurs as a consequence of the limitations of the model that we correctly use to extract optical properties. The diffusion based model of light transport used here assumes a semi-infinite homogeneous medium. While this seems to be a reasonable assumption for wavelengths longer than 700 nm, as evidenced by the behavior of the scattering coefficient at wavelengths corresponding to high water absorption, it is clearly incorrect at wavelengths corresponding to chlorophyll absorption. Apples are a two-layer medium consisting of an outer skin layer containing chlorophyll and an inner region consisting of pulp. The thin chlorophyll layer can be highly absorbing depending on the ripeness of the apple. When measuring apples of distinctly different ripeness, we observed a direct correlation between the scattering dip amplitude and the magnitude of the chlorophyll absorption peak at 670 nm. This correlation indicates an incomplete separation of the recovered optical properties for high concentrations of chlorophyll. With more detailed accounting for effects of the thin chlorophyll layer in the model, we should be able to completely separate the scattering from absorption for chlorophyll.

Figure 12:
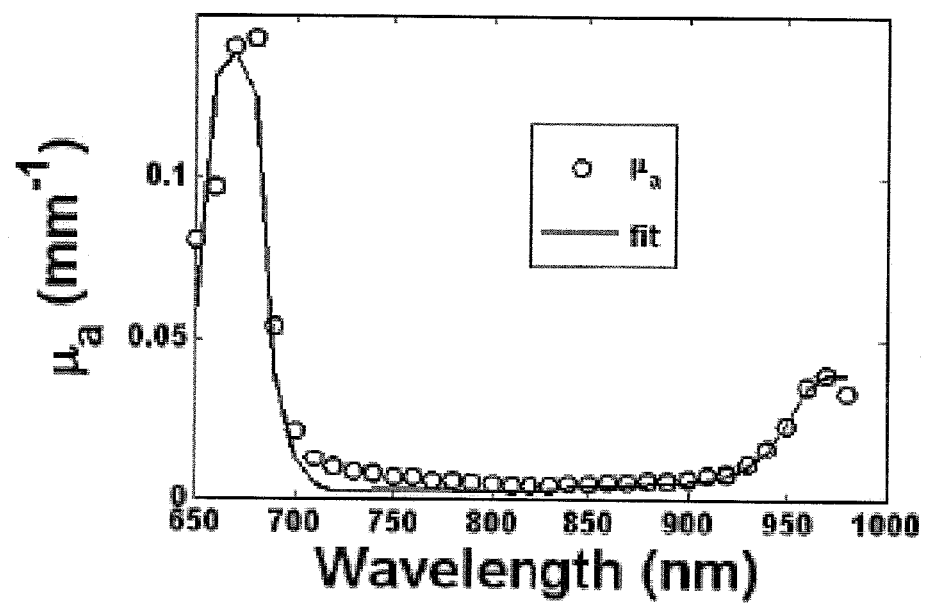
FIG. 12 is a graph of an SFDI absorption spectral fit (solid line) to the data (open circles) for water and chlorophyll for Golden Delicious apple (0.315 J level bruised region). The water percentage is 80.9% and chlorophyll concentration is 28.9 μM.

To quantify the percentage volume of water and the amount of chlorophyll in the apples, the absorption spectrum was fitted with a linear (Beer's law) summation of individual line shapes of chromospheres (water and chlorophyll) absorption contributions:

$$\mu_a(\lambda) = 2.303 \sum_{i=1}^{2} c_i \varepsilon_i(\lambda)$$

Where $c_i$ and $\varepsilon_i(\lambda)$ represent chromophore concentrations and molar extinction coefficients, respectively. FIG. 12 shows a spectral fit on the 0.0315 J level bruised region. Using reported extinction coefficients of water and chlorophyll, the equation above was inverted to calculate chromophore concentration at each pixel by linear fitting to the multi-spectral absorption images. The percentage of water calculated is 80.9% and the chlorophyll concentration is 28.9 μM.

Figure 13A:
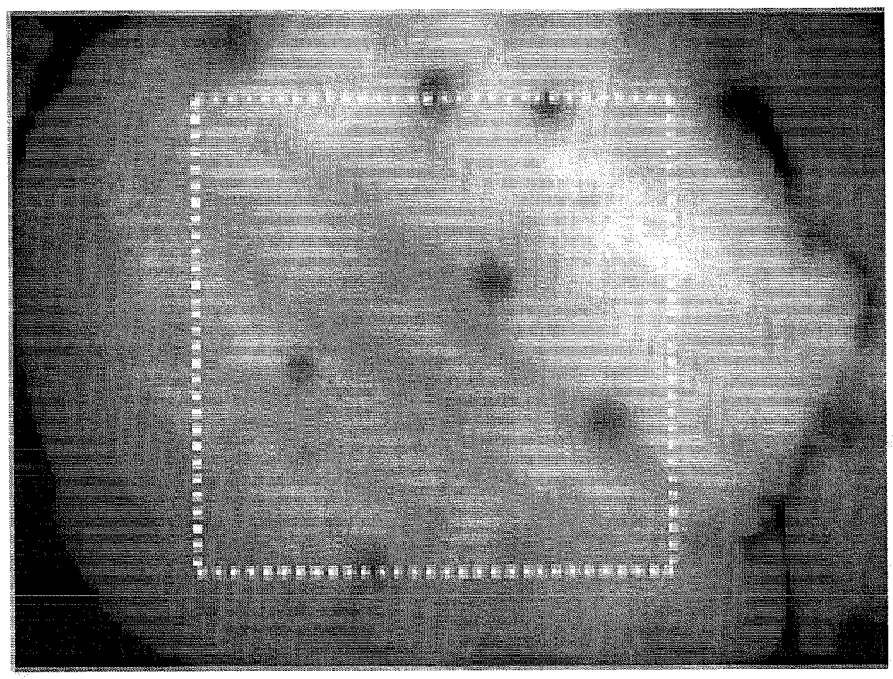
FIGS. 13a-13d are Golden Delicious apple SFDI spatial results for 0.06 J level bruises.
Figure 13B:
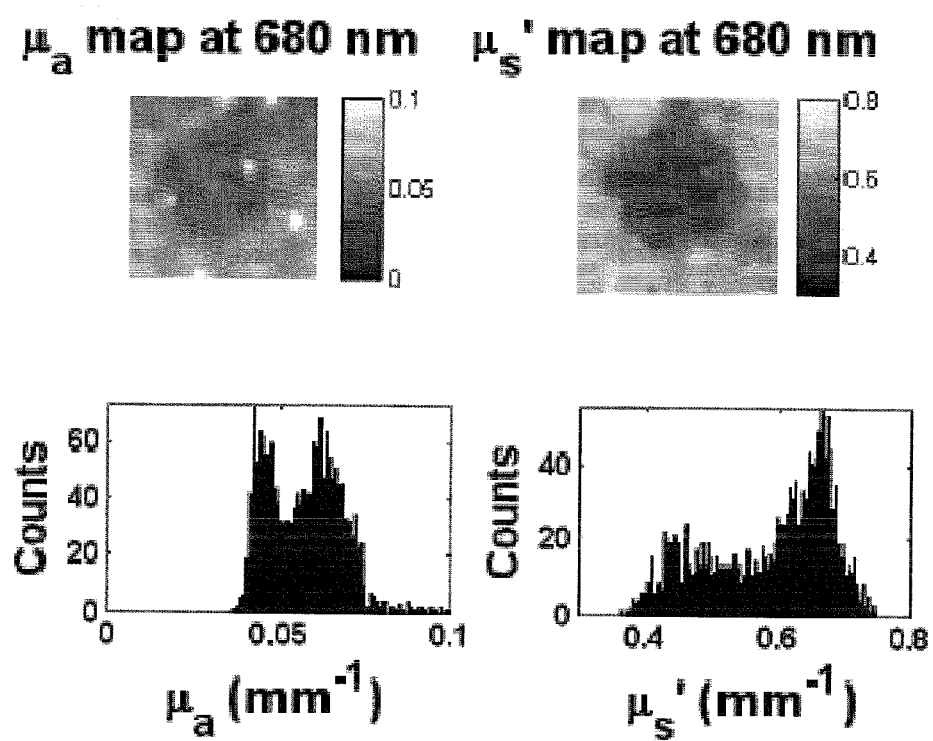
Figure 13C:
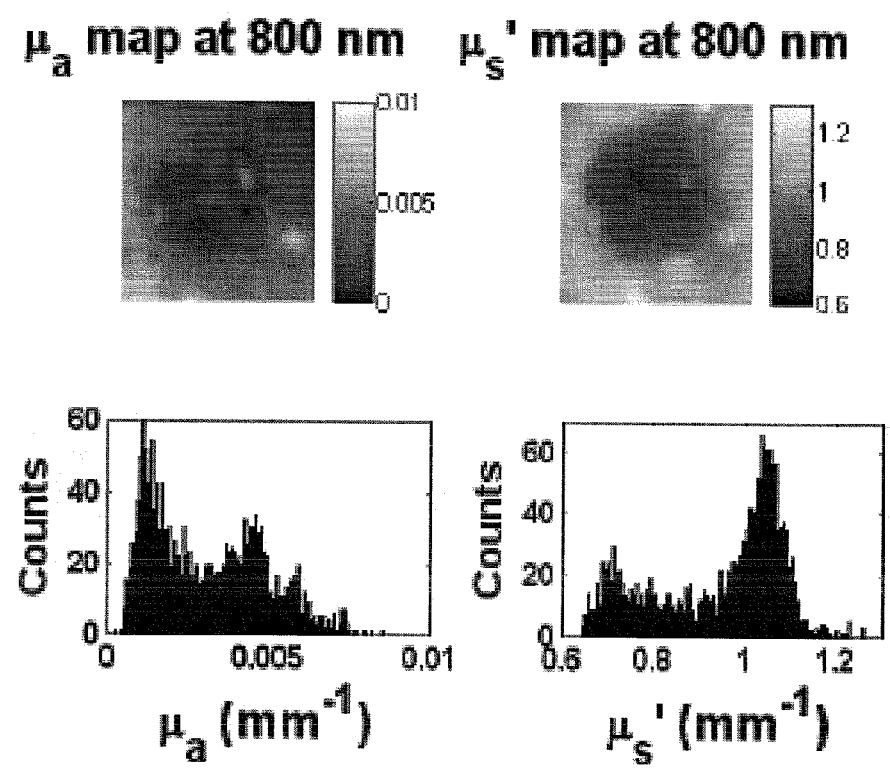
Figure 13D:
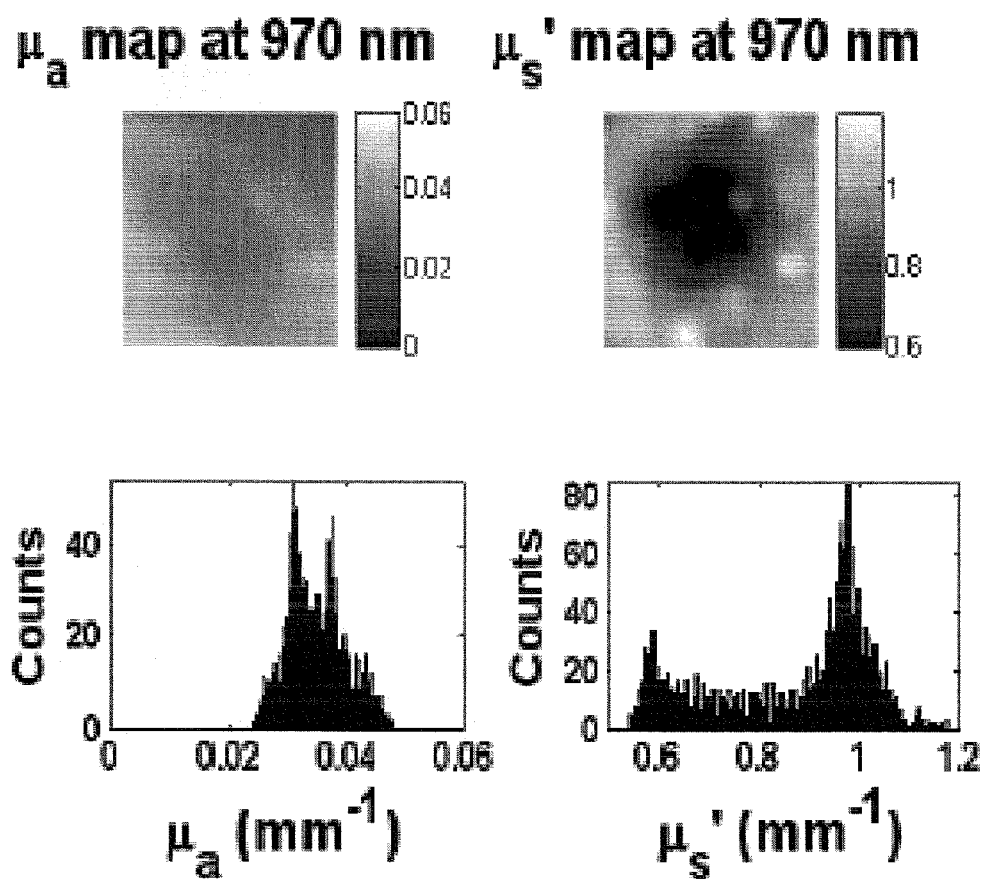

FIGS. 13a-13d show SFDI spatial maps for a lower bruised level (0.06 J level) for three (680 nm, 800 nm, and 970 nm) of the 32 wavelength images obtained. FIGS. 13a-13d are similar to FIGS. 10a-10d except that the energy used to create the bruise is much less (0.06 J), and the Golden Delicious apple was a different apple. FIG. 13a shows a reflectance image (680 nm) with the ROI (dotted rectangle) before SFDI image analysis of the bruised and non-bruised region. The bruised region is visible within the ROI as a dark area. The dark spots are apple lenticels, which were observed visually with no instrumentation. The bruise diameter, approximately 8 mm, was determined by measuring the diameter of the indentation caused by the impact. The depth of the bruise, approximately 3 mm, was determined by slicing out a cross section of the bruised region and measuring the depth of the discoloration from the surface. FIGS. 13b, 13c, and 13d contain spatial maps in the top portions of the figures of the spatially resolved absorption and scattering properties that were obtained by performing a frequency fit at each CCD pixel. To the right of each image is a vertical grey scale (mm−1). As the magnitude of the absorption or scattering coefficient increases, the map shifts from black to grey and finally, white. The bruise region is clearly visible in all three scattering images in the top right of FIGS. 13b, 13c and 13d. The circular bruised region has lower scattering coefficients than the non-bruised outer region. Also, the bruised region is visible in all three absorption images in the top left of FIGS. 13b, 13c, 13d. At the bottom of each spatial map is a histogram obtained from all pixels within the total ROI. The vertical axis indicates the frequency of occurrence of the magnitude of the absorption or scattering coefficient (horizontal axis) determined at each pixel. As in FIGS. 10a-10d there are two distributions; one for the non-bruised region (low scattering coefficients), and one for the bruised region (high scattering coefficients). In contrast, the bruised distribution height is much less than the non-bruised region. Similarly to FIGS. 10a-10d, the bright white dots in the images are from the apple lenticels.

Comparing the histogram for the 0.06 J bruise in FIGS. 13b, 13c, and 13d with the histograms for the 0.314 J bruise in FIGS. 10b, 10c, and 10d, a correlation can be seen between the energy used to induce bruising and the ratio of the bruise pixel-count area to the non-bruise pixel-count area. For example, in FIG. 10c at 800 nm the scattering pixel-count area for the 0.314 J bruise is almost the same as the scattering pixel-count area for the adjacent non-bruised region. On the other hand, in FIG. 13c for the 0.06 J bruise, the scattering pixel-count area is much lower than the non-bruised pixel-count area. The ratio of the pixel count area for bruised to non-bruised regions could be used to quantify the bruise severity in apples.

Figure 14A:
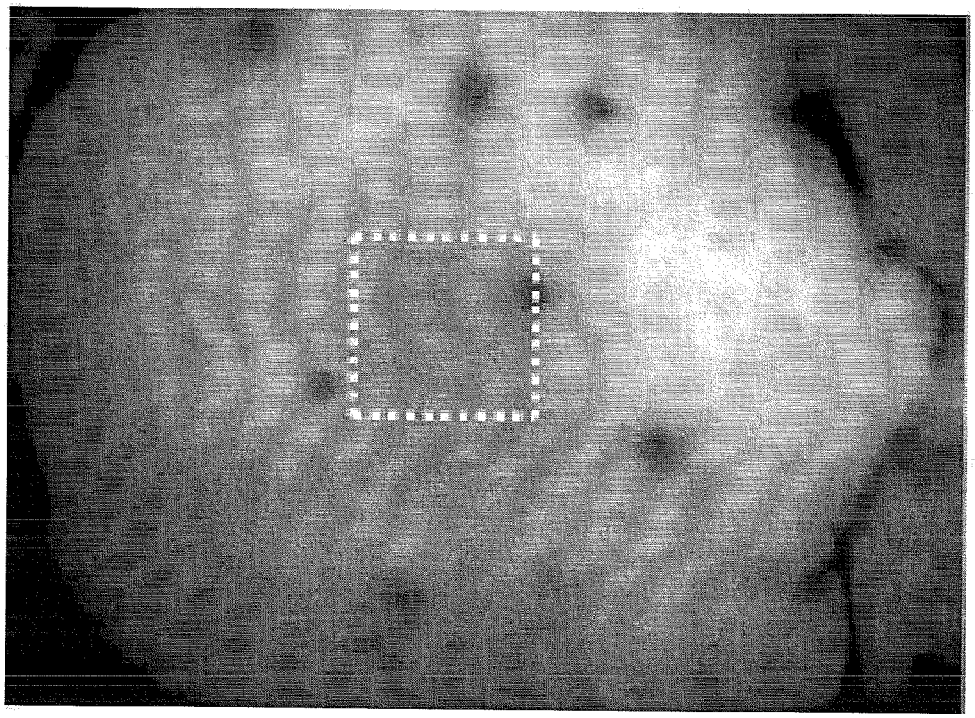
FIGS. 14a-14d are Golden Delicious apple SFDI average absorption and scattering spectra results for 0.06 J level bruises.
Figure 14B:
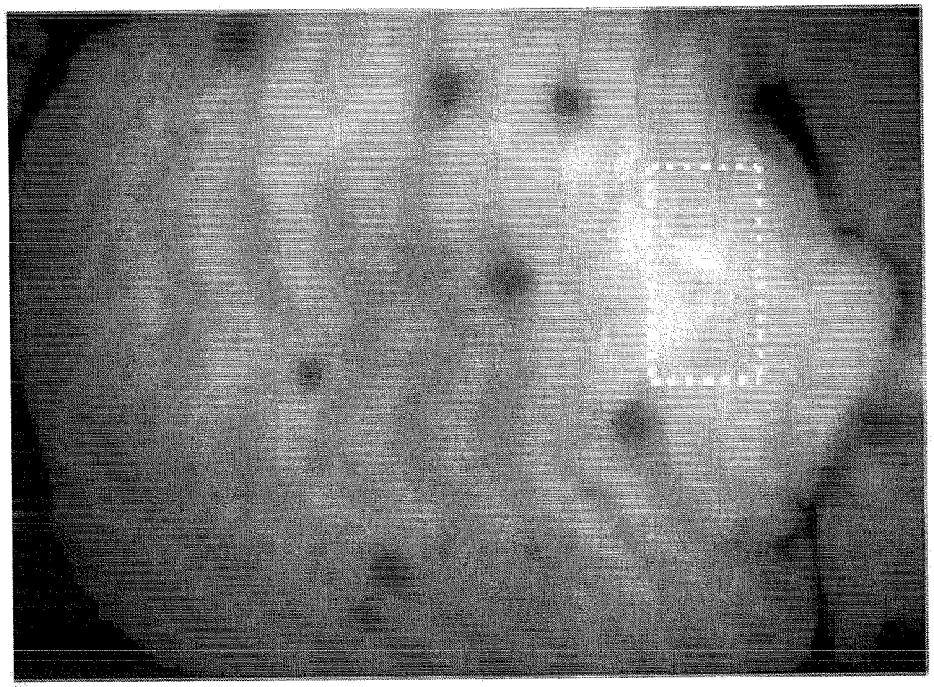
Figure 14C:
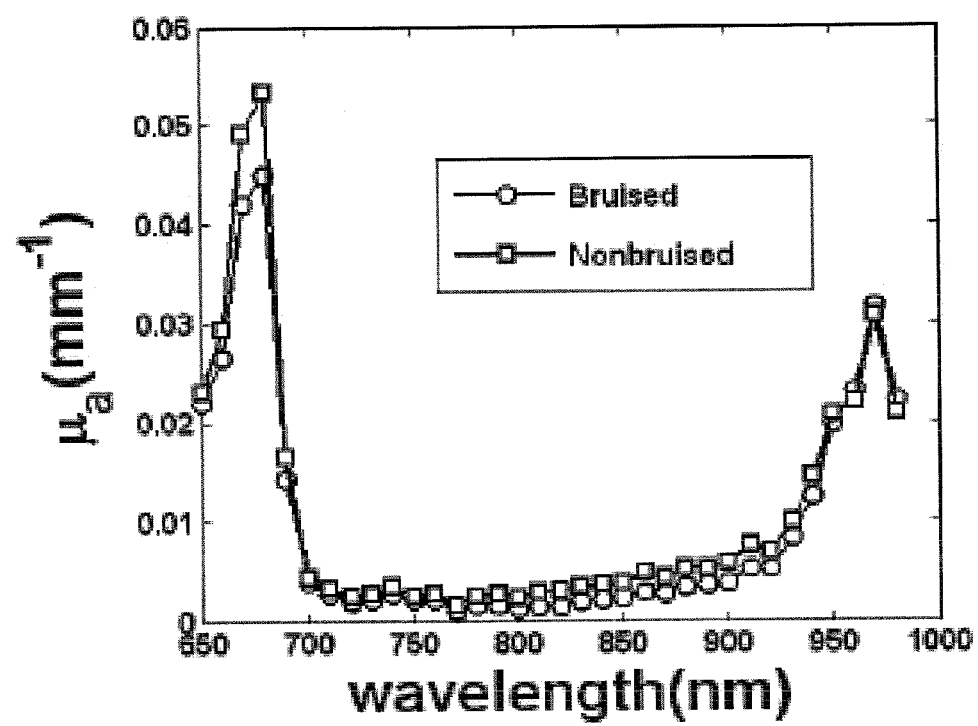

FIGS. 14a-14d show SFDI absorption and scattering spectra from 650 nm to 980 nm for a bruised (0.06 J level) and non-bruised region on the same Golden Delicious apple as in FIGS. 13a-13d. FIG. 14a is a reflectance image at 680 nm with the bruised ROI (dotted rectangle), and FIG. 14b is a reflectance image at 680 nm with a near-by non-bruised ROI (dotted rectangle) on the same Golden Delicious apple as shown in FIG. 13a, 13b, and 13d Calculated absorption spectra for the bruised and non-bruised ROI are shown in FIG. 14c. The bruised and non-bruised plots are very similar, which is expected since bruising is mainly a structural change in the apple at these wavelengths. Similarly to FIGS. 11a-11d, both absorption spectra are dominated by two peaks; one centered near 970 nm from water and a second peak centered around 675 nm from chlorophyll a.

Figure 14D:
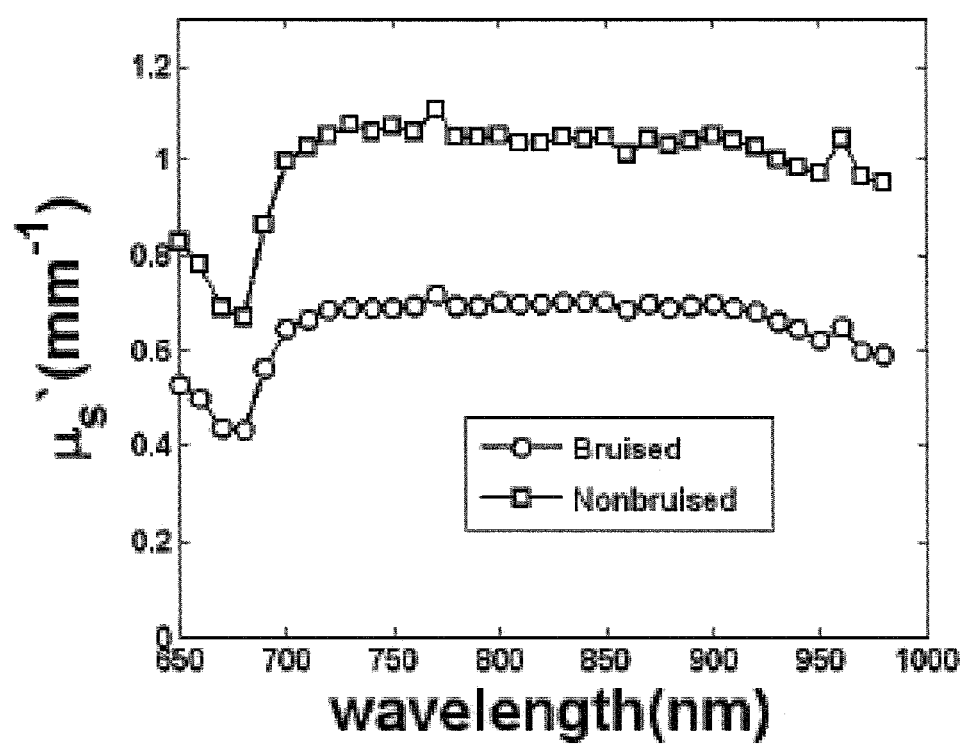

Calculated scattering spectra for the bruised and non-bruised ROI are shown in FIG. 14d. There is a large change in the scattering coefficients between the bruised and non-bruised regions. From 700 nm to 980 nm, the non-bruised mean scattering coefficient is approximately 1.05 mm−1 with a standard deviation of 0.018, whereas the bruised mean scattering coefficient is approximately 0.7 mm−1 with a standard deviation of 0.035. FIG. 14d shows a dip in the scattering coefficients near 675 nm for both the bruised and non-bruised regions, but the dip size is smaller than was seen in FIG. 14d. This smaller size is attributed to the smaller chlorophyll magnitude as associated with the smaller absorption coefficient magnitude at 670 nm (0.065 mm−1) in FIG. 14c as compared to the larger absorption coefficient magnitude at 670 nm (0.0.14 mm−1) in FIG. 11c. Although the average scattering coefficients are different for the two bruised regions and for the two non-bruised regions, the ratio of the average scattering coefficients for the bruise region to the average scattering coefficients for the non-bruise is approximately equal. For example, at 800 nm, the average scattering coefficient ratio for the 0.06 J bruise to non-bruise region is 0.67, and the ratio for the 0.315 J bruise is 0.677. This indicates that the relative change in the damaged cell structure is almost the same for these two levels of energy used to induce bruising. On the other hand, the severity of bruising is distinguishable by comparing the scattering pixel-count area for the bruise region to non-bruise region (FIGS. 10a-10d and 13a-13d).

Thus, it can be now be understood that a non-contact, optical imaging technology known as SFDI can be used for the detection of bruising and quantification of bruise severity on Golden Delicious apples. Quantitative absorption and scattering image maps from 650 to 980 nm were obtained for bruises that were induced using energies of 0.06 J and 0.314 J. Bruising induced using 0.06 J is distinguishable from those induced using 0.314 J. Furthermore, regions damaged by bruising are clearly discernable from surrounding non-bruised region. The average scattering and absorption spectra were calculated for the two levels of bruise severity and compared to those obtained for adjacent non-bruised regions. For the 0.314 J bruised apple, the non-bruised mean scattering coefficient was 1.3 mm−1 (800 nm) whereas the bruised region mean scattering coefficient was 0.88 mm−1 (800 nm). For the 0.06 J bruised apple, the non-bruised mean scattering coefficient was 1.05 mm−1 (800 nm) whereas the bruised mean scattering coefficient was 0.7 mm−1 (800 nm) To our knowledge this is the first report of wide-field imaging of quantitative optical properties in the spatial-frequency domain oriented around bruising in apples. It is contemplated as within the scope of the invention that more sophisticated modeling with sample curvature correction for entire apple images. In addition, the quantitative relationship between spatially resolved absorption and reduced scattering coefficients and the chemical and physical properties of apples that are traditionally used to assess quality (e.g. firmness, ripeness) can be derived using the methodology of the invention.

SFDI has the potential for rapidly (two spatial frequencies and one or two optimized wavelengths) and inexpensively detecting and quantitatively mapping bruising on apples over a wide field-of-view. The SFDI instrument is based on an innovative illumination scheme that produces data that, when interpreted with appropriate models of light propagation, yields both spatially resolved and bulk absorption and reduced scattering coefficients over a large field of view in a single measurement. The technique can simultaneously extract subsurface features from a turbid target of interest. By employing a broadband source of illumination with a liquid crystal tunable filter or a rotating filter wheel 30, we can quantitatively extract chemical information from the wavelength-dependent optical properties. The biochemical changes that accompany fruit ripening and bruising provide spectral contrast.

In conclusion, we have demonstrated a potentially rapid (with reduced wavelengths and spatial frequencies that have been optimized for a particular target fruit) and inexpensive technique for achieving quantitative optical property mapping in fruit over a wide field-of-view. It is anticipated that more sophisticated modeling with sample curative correction for entire fruit images can be readily practiced. In addition, investigations are under way that focus on the quantitative relationship between spatially resolved absorption and reduced scattering coefficients and the chemical and physical properties of fruit that are traditionally used to assess quality (e.g. firmness, sugar content, bruising).

This technique produces a detailed quantitative picture of composition and defect identification using non-invasive and non-ionizing means. Existing optical methods used in fruit assessment typically do not attempt to separate and quantify absorption and scattering in-situ. Wet-chemical analysis methods, while generally quantitative, are usually destructive and require sample removal, dilution, and separation. In addition, chemical analysis cannot provide information on how multiple components interact in their native state. The use of combined SFDI with fluorescence imaging in an agriculture oriented context is valuable in basic studies conducted by scientists in academic, government, and commercial sectors.

Because of its many potential uses, the SFDI and fluorescence technology has a broad impact in both the biomedical and agricultural domains. While the existing SFDI apparatus is designed to operate in the 400-1100 nm spectral window, the method can be translated, with appropriate choice of source and sensor, to other spectral domains. For example, with an InGaAs sensor array and use of quantum cascade laser technology SFDI can be conducted in the spectral range from 1100-2400 nm, which would allow one to capture additional metabolic information related to sugars, carbohydrates and lipids.

For example, the banana and apple quality evaluation as well as fecal contamination detection on apples can be quantitatively performed, namely using SFDI chlorophyll-fluorescence for the objective assessment of quality in bananas and apples, and assessment of fecal contamination on apples. The design information can be used to build imaging inspection systems for sorting bananas and apples based on surface and internal attributes of quality.

This optical imaging technique uses multi-spatial frequencies for quantitatively determining the absorption, scattering and chlorophyll fluorescence properties of media in the near-infrared region between 400 nm and 1100 nm. In addition, this technique can measure or map the depth sensitive distribution.

This capability is used for the following objects. The absorption, reduced scattering coefficients, and chlorophyll fluorescence properties is then correlated with conventional quality attributes for bananas and apples, and fecal contamination on apples. The quantitative banana surface and subsurface optical properties, and chlorophyll fluorescence are deduced using SFDI chlorophyll-fluorescence correlate to the peel chlorophyll content, subsurface pulp firmness, and pulp sugar content over a large field of view. The relationship between peel chlorophyll content and pulp sugar content is determined. The relationship between peel chlorophyll content and pulp firmness is determined. The quantitative apple surface and subsurface optical properties, and chlorophyll fluorescence are deduced using SFDI chlorophyll-fluorescence correlate to firmness, sugar content, and bruised apple tissue over a large field of view. The quantitative apple surface and subsurface optical properties, and chlorophyll fluorescence are deduced using SFDI chlorophyll-fluorescence correlate to fecal contamination. The depth sectioned imaging that is conferred by SFDI chlorophyll-fluorescence is used to improve fecal contamination detection.

Therefore, the illustrated embodiment can be understood to contemplate: 1) correlation between banana quality (ripeness, pulp firmness and pulp sugar content) and spatially resolved SFDI optical properties, and chlorophyll fluorescence; 2) correlation between apple quality (ripeness, firmness, sugar content, bruising) and spatially resolved SFDI optical properties, and chlorophyll fluorescence, 3) correlation between apple fecal contamination and spatially resolved SFDI optical properties, and chlorophyll fluorescence.

The SFDI instrument at the Beckman Laser Institute is used to acquire image data. A filter wheel 30 containing bandpass filters is used to provide spectral selectivity in combination with the broadband light source that is currently in place. Spectral coverage from 400 to 1100 nm is obtained using a combination of liquid crystal tunable filter (Nuance system, Cambridge Research Inc, Woburn Mass.) with the rotating filter wheel. The Nuance system at BLI is optimized to work over the region from 400-720 nm. It is configured to allow serial combination with a rotating filter wheel 30 which can be used to sweep through the 500-1100 nm range. Images are obtained for each spectral window as the spatial frequency of the illumination is swept. To operate the SFDI instrument for chlorophyll fluorescence measurements, there must be a separation of the fluorescence signal from the much stronger excitation light. This is achieved with the use of a optical short pass filters for the excitation source, and a long pass filters to protect the detector system from stray excitation light, while allowing passage of the longer wavelength fluorescence signal. Fluorescence excitation between 410 nm and 430 nm is used to obtain maximum fluorescence yields for the banana, apple, and animal feces measurements.

In all cases for which SFDI fluorescence data is acquired, a digital color image is also acquired in order to provide a frame of reference and so that we can qualitatively illustrate the sensitivities of the SFDI chlorophyll-fluorescence method compared to simple color imaging.

Banana samples free from blemishes and bruises are acquired from local supplies selected with different stages of ripeness as determined by visual color assessment. The color of each banana is evaluated subjectively by comparing the fruit with a standard color chart to obtain banana maturity ratings for each fruit. A scale of 1-7 is generally accepted: 1 is green, 2 is green with trace of yellow, 3 is more green than yellow, 4 is more yellow than green, 5 is yellow with green tips, 6 is all yellow, 7 is yellow with brown spots.

In addition, bananas free from blemishes and bruises are obtained from produce companies or banana distributors (Valley Fruit and Produce Co., Los Angeles, Calif.) that ripen bananas for controlled ripening measurements. Green bananas are placed in desiccators containing ethylene producing substances such as apples. Banana ripening are examined over several hundred hours. All bananas are equilibrated to room temperature (25° C.) before testing.

Each banana is placed on a sample holder and positioned horizontally. Four measurements per banana is selected for SFDI chlorophyll-fluorescence image acquisition with two equally spaced locations along the center on each side. At each location, a combination of filter wheel and liquid crystal tunable filter is used to obtain multiple wavelength spectral and fluorescence images. For each wavelength band, the spatial frequency of the illumination is swept as discussed above. The banana is then turned over and the measurements repeated on the two locations.

After completing the imaging, the peel is removed in order expose the pulp. Conventional measurements are performed using a Magness-Taylor firmness tester at each of the four image locations. Measurements of firmness are compared to the spatially resolved absorption and reduced scattering coefficients, and chlorophyll fluorescence properties deduced from SFDI chlorophyll-fluorescence measurements. Because reduced scattering coefficient is related to structural matrix, there should be a significant correlation between the magnitude of scattering and traditional firmness. In addition, because firmness is related to ripeness, there should be a significant correlation between the magnitude of chlorophyll florescence and firmness.

After completing the imaging, conventional refractometry is used to measure the sugar concentration at the same four SFDI chlorophyll-fluorescence image locations. Specifically, pulp juice is extracted, and its sugar value measured using a digital refractometer (Dadzie and Orchard 1997). Measurements of sugar content are compared to the spatially resolved absorption and reduced scattering coefficients and chlorophyll fluorescence properties deduced from SFDI chlorophyll-fluorescence measurements. Because chlorphyll is related to ripeness, there should be a significant inverse correlation between the magnitude of chlorphyll fluorescence and traditional pulp sugar content. In addition, there should be a correlation between scattering coefficients and sugar content because of the relationship of pulp firmness with sugar content. Pulp firmness and sugar content are both related to banana ripenness. Pulp firmness decrease and sugar content increases during ripening.

After completing the imaging, conventional measurements were performed using a Magness-Taylor firmness tester at each of the four image locations. Measurements of firmness were compared to the spatially resolved absorption and reduced scattering coefficients deduced from SFDI measurements. Because reduced scattering coefficient is related to structural matrix, there should be significant correlation between the magnitude of scattering and traditional firmness.

The procedure outlined in the firmness measurements is used for collecting image data. Conventional technology is used to measure the sugar concentration at the same four SFDI chlorophyll-fluorescence image locations. Specifically, juice is extracted, and its sugar value measured using a digital refractometer. Measurements of sugar content is compared to the spatially resolved absorption and reduced scattering coefficients and chlorophyll fluorescence properties deduced from SFDI chlorophyll-fluorescence measurements. Because chlorphyll is related to ripeness, there should be a significant inverse correlation between the magnitude of chlorphyll fluorescence and traditional sugar content. In addition, there should be a correlation between scattering coefficients and sugar content because of the relationship of firmness with ripening.

The procedure outlined in the apple firmness measurements is used for collecting image data. After completing the imaging, bruises were applied to the four locations. In order to capture a variety of subtlety of bruising, additional data is acquired via SFDI chlorophyll-fluorescence imaging while varying the severity of bruise. To accomplish this, a device is used that was built that will enable the application of a measured and reproducible amount of force to induce bruising on an apple. The device consists of a long hollow tube mounted vertically on a platform. A steel disk is inserted in the tube at a predetermined height and released for impact on an apple mounted below on the platform. An apple is placed on a holder with the stem end-calyx axis positioned horizontally. SFDI chlorophyll-fluorescence images were acquired prior to the induction of bruises. The falling disk will subsequently be employed to impact the apple to produce a controlled bruise.

This process is repeated on the other three locations. Different amounts of bruising is induced by varying the height of the disc release. After bruises were induced at the four locations, SFDI chlorophyll-fluorescence images were retaken at the four locations. Optical properties before and after bruising is deduced from SFDI chlorophyll-fluorescence data and compared. Spectrally resolved optical properties were analyzed in order to determine the wavelength regions that may be the most sensitive reporters of damage. In addition, depth sectioned images were deduced from SFDI chlorophyll-fluorescence data as described in order to assess sensitivity of the technique to recording subsurface damage.

The procedure outlined above is used for collecting image data. After completing the imaging, fecal matter is applied to the four locations. The fluorescence excitation source wavelength is centered at 418 nm, which produces the best contrast at 670 nm emission between feces contaminated spots and apples surfaces. Other wavelengths that is investigated is centered at 680, 685, and 730 nm.

Fresh cow feces from animals fed feedstuffs containing green roughage is acquired from local dairy farms (Riverside County, Calif.) and diluted 1:10 by weight with distilled water. Feces contaminated spots on apples is created by applying diluted cow feces with distilled water (three concentrations, 1:20, 1:50 and 1:100 by weight). Using a pipette, 30 µl of each dilution of cow feces is applied to the four sides. Three concentrations is applied to each side in a equally spaced circular pattern; starting 1:20 on upper left, followed by 1:50 and 1:100 dilutions, respectively, in a clockwise direction.

After the fecal matter application, SFDI chlorophyll-fluorescence images were retaken at the four locations. Optical properties before and after fecal matter application were deduced from SFDI chlorophyll-fluorescence data and compared. Spectrally resolved optical properties were analyzed in order to determine the wavelength regions that may be the most sensitive reporters of contamination. In addition, depth sectioned images is deduced from SFDI chlorophyll-fluorescence data as described in order to assess sensitivity of the technique to recording subsurface contamination. SFDI chlorophyll-fluorescence provides better fecal contamination detection. By using depth sectioning to limit the light excitation to the fecal layer on the apple surface the fecal matter fluorescence is enhanced over background fluorescence from the uncontaminated part of the apple.

The SFDI system is also able to record spatially resolved images of: 1) chlorophyll fluorescence, 2) absorption coefficient and 3) reduced scattering coefficients in banana tissue. These basic studies were conducted using the existing BLI SFDI system, with the addition of a 450 nm (40 nm bandwidth) excitation filter (Andover Corp.). This set of experiments is intended only to illustrate simple feasibility of combined SFDI with fluorescence imaging. We also demonstrate which is not optimized for chlorophyll fluorescence investigation.

Figure 7:
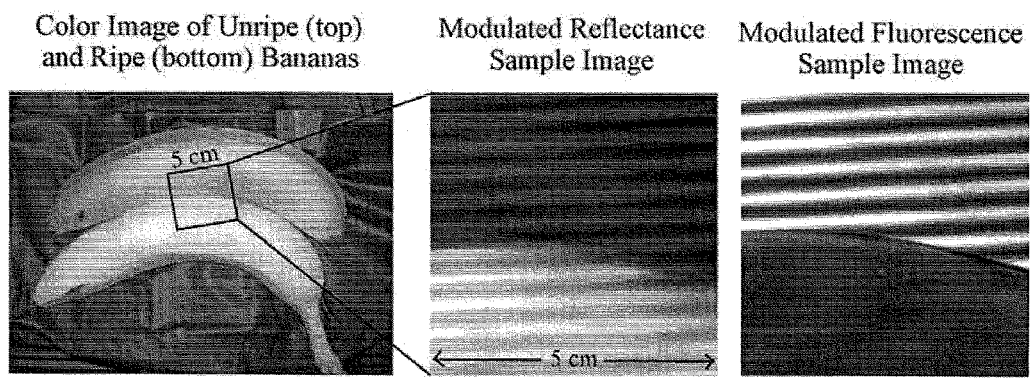
FIG. 7 is a series of photographs which shows on the left a color image of unripe and ripe bananas (top and bottom, respectively) showing region of interest for SFDI measurement. To the right: samples of modulated reflectance (middle) and fluorescence (right) at 680 nm with a spatial period of approximately 5 mm (spatial frequency=0.2/mm) are shown.

SFDI measurements of fluorescence, absorption, and scattering optical properties of fruit were performed on unripe and ripe bananas. Spatial modulation data were collected at 23 evenly-spaced frequencies between 0 and 0.21 $mm^{-1}$ over a 5×5 cm field-of-view. Reflectance mode imaging was performed using single bandpass filters at 450 nm and 680 nm (20 nm bandwidths), corresponding to regions near the excitation and emission regions of the chlorophyll spectrum, respectively. Fluorescence measurements were performed using 450 nm illumination from bandpass filtering of the white light source and 680 nm detection. In FIG. 7, left, we show a color image of two adjacent unripe and ripe bananas, top and bottom, respectively. The black box drawn shows the approximate region of interest used for subsequent SFDI measurements. This 5 cm×5 cm field-of-view is a consequence of the lens system of the existing camera, but can be expanded up to approximately 50 cm square without significant loss of measurement sensitivity. To the right, we show sample raw reflectance (middle) and fluorescence (right) modulated data for an illumination spatial frequency of 0.21 $mm^{-1}$ (approximately 5 mm spatial period).

Figure 8:
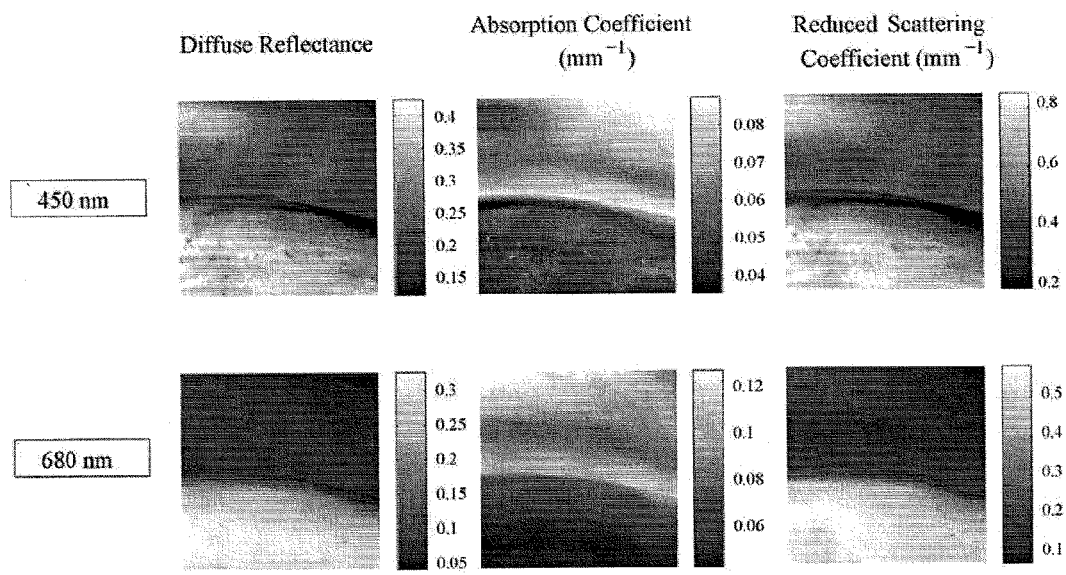
FIG. 8 is a series of photograph showing diffuse reflectance maps (left), quantitative absorption maps (middle, $mm^{-1}$), and quantitative reduced scattering maps (right, $mm^{-1}$) of banana at excitation (450 nm, top) and emission (680 nm, bottom) wavelengths. Note the large contrast of unripe and ripe banana (top and bottom of image, respectively) in all quantities, conveying differences in chlorophyll concentration (absorption contrast) and tissue matrix structure (scattering contrast).

Pixel-by-pixel demodulation of spatial frequency reflectance data allows spatial mapping of the absorption coefficients at the excitation and emission wavelengths. In FIG. 8, we show calibrated planar diffuse reflectance maps (left), and calculated quantitative absorption and reduced scattering coefficient maps (middle and right, $mm^{-1}$) of the unripe and ripe bananas (top and bottom of image, respectively). Notice the large contrast of unripe and ripe banana in all quantities, conveying differences in chlorophyll concentration (absorption contrast) and tissue matrix structure (scattering contrast).

Figure 9:
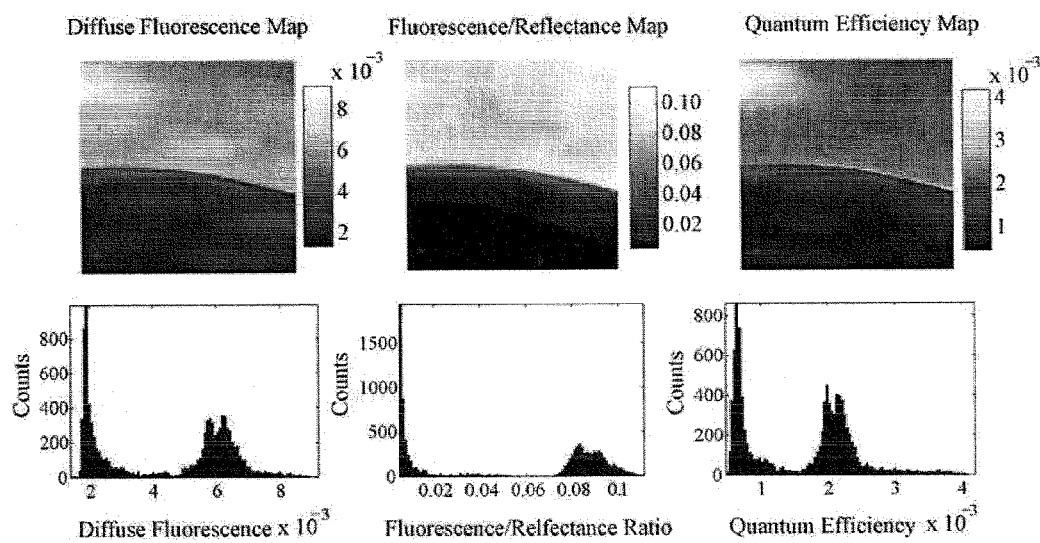
FIG. 9 is a series of maps (top) and corresponding pixel histograms (bottom) of calibrated diffuse fluorescence (left), diffuse fluorescence/reflectance ratio (center), and quantum efficiency (right) measured for unripe and ripe banana (image top and bottom, respectively).

Finally, in FIG. 9, we show three different representations of the fluorescence optical properties (top), along with corresponding image pixel histograms (bottom). First, on the left we have the calibrated diffuse fluorescence, demonstrating striking contrast in the fluorescence yield from the two samples. Notice, however, the large degree of spatial heterogeneity in the emitted fluorescence. This is due to spatial variation of the absorption and scattering properties, perturbing light transport at both excitation and emission wavelengths. A simple, qualitative (relative) method for flat-fielding this effect is to divide by the excitation diffuse reflectance (FIG. 9, middle). However, this method does not allow for quantitative comparison of samples, preventing use of absolute metrics of ripeness and the possible presence of nonlocalized contamination. Through the use of SFDI, we can quantitatively assess the fluorescence quantum yield and fluorophore species concentrations. This is done by model-based prediction of fluorescence using the absolute absorption and scattering properties determined from SFDI reflectance measurements. Comparison of the measured diffuse fluorescence with this model allows quantification of the fluorescence quantum yield of the sample (FIG. 9, right). This calculation assumes the predominant absorber at 450 nm is chlorophyll. Incorporation of additional reflectance wavelengths in the visible range would further enable separation of the absolute concentrations of the various absorbing molecules, and allow a correspondingly more accurate measurement of fluorescence quantum yield.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example, while the disclosed method can be used to grade produce; it may also be practiced as the method may be used to assess grade (ripeness, bruising, disease) of fruit, both in a post-harvest sense as well as having a field deployable version of the apparatus that can be taken into orchards and fields in order to optimize i) time of picking ii) fertilization and hydration and iii) screening for diseased trees etc. It may be also useful for assessing damage resulting for changes in weather conditions (soft-freeze vs. hard-freeze). The method may also be used in a post-harvest sense to optimize the ripening process; for example, with banana crops, it is often necessary to ripen batches of bananas via exposure to ethylene gas. The increasing ripeness of bananas is accompanied by change in the chromophore composition in the banana skin; specifically the chlorophyll concentration decreases with increasing ripeness; we can objectively assess this using spatially resolved maps of chlorophyll absorption via modulated imaging as well as quantitative changes in spatially resolved fluorescence.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An improvement in grading or assessing produce, fruit or vegetables comprising:
noninvasively and quantitatively determining spatially resolved absorption and reduced scattering coefficients over a wide field-of-view of a food object using spatial-frequency-domain imaging (SFDI); and
simultaneously imaging fluorophore spectral characteristics of the food object.

2. The method of claim 1 further comprising imaging to identify surface characteristics or depth sectioned imaging of subsurface characteristics of the food object.

3. The method of claim 2 where depth sectioned imaging comprises assessing depth sensitivity as a function of source spatial frequency, wavelength selection and/or amplitude modulation to provide subsurface imaging/tomography.

4. The method of claim 1 further comprising imaging to identify surface characteristics and depth sectioned imaging of subsurface characteristics of the food object.

5. The method of claim 1 further comprising separating average background optical properties from heterogeneity components from a single image of the food object.

6. The method of claim 1 further comprising separating average background fluorescence from a target fluorescence feature using selection of spatial frequency of illumination from a single image of the food object.

7. The method of claim 1 further comprising separating a superficial fluorescent feature from a deep fluorescent feature based on selection of spatial frequency of illumination from a single image of the food object.

8. The method of claim 1 where quantitatively determining spatially resolved absorption and reduced scattering coefficients comprises quantitative fluorescence imaging to deconvolve the effects of scattering and absorption from fluorophore spectra.

9. The method of claim 1 where quantitatively determining spatially resolved absorption and reduced scattering coefficients over a wide field-of-view of a food object comprises performing both diffuse optical tomography and rapid, wide-field quantitative mapping of optical properties within a single measurement platform.

10. The method of claim 1 where quantitatively determining spatially resolved absorption and reduced scattering coefficients over a wide field-of-view of a food object further comprises determining therefrom pulp firmness, sugar content, bruise sensitivity, or fecal contamination of the food object.

11. The method of claim 1 where quantitatively determining spatially resolved absorption and reduced scattering coefficients over a wide field-of-view of a food object further comprises quantitatively determining severity of bruising in the food object by quantitative assessment of the mean scattering coefficient of a bruised region.

12. An apparatus for noninvasively and quantitatively determining spatially resolved absorption and reduced scattering coefficients over a wide field-of-view of a food object, including fruit or produce, using spatial-frequency-domain imaging (SFDI) comprising a single modulated imaging platform comprising:
a light source comprising a preselected spectral domain;
a digital micromirror optically coupled to the light source to control a modulated light pattern directed onto the food object at a plurality of selected spatial frequencies;
a multispectral camera for taking a spectral image of a reflected modulated light pattern from the food object;
a spectrally variable filter optically coupled between the food object and the multispectral camera to select a discrete number of wavelengths for image capture; and
a computer coupled to the digital micromirror, camera and variable filter to enable acquisition of the reflected modulated light pattern at the selected spatial frequencies, wherein the computer controls the digital micromirror camera and variable filter to simultaneously image fluorophore spectral characteristics of the food object.

13. The apparatus of claim 12 where the computer controls the digital micromirror, camera and variable filter to identify surface characteristics or depth sectioned imaging of subsurface characteristics of the food object.

14. The apparatus of claim 12 where the computer controls the digital micromirror, camera and variable filter to separate average background optical properties from heterogeneity components from a single image of the food object.

15. The apparatus of claim 12 where the computer controls the digital micromirror, camera and variable filter to separate average background fluorescence from a target fluorescence feature using selection of spatial frequency of illumination from a single image of the food object.

16. The apparatus of claim 12 where the computer controls the digital micromirror, camera and variable filter to separate a superficial fluorescent feature from a deep fluorescent feature based on selection of spatial frequency of illumination from a single image of the food object.

17. The apparatus of claim 12 where the computer controls the digital micromirror, camera and variable filter to assess depth sensitivity as a function of source spatial frequency, wavelength selection and/or amplitude modulation to provide subsurface imaging/tomography.

18. The apparatus of claim 12 where the computer controls the digital micromirror, camera and variable filter to deconvolve the effects of scattering and absorption from fluorophore spectra.

19. The apparatus of claim 12 where the computer controls the digital micromirror, camera and variable filter to perform both diffuse optical tomography and rapid, wide-field quantitative mapping of optical properties within a single measurement platform.

20. The apparatus of claim 12 where the computer controls the digital micromirror, camera and variable filter to determine pulp firmness, sugar content, bruise sensitivity, or fecal contamination of the food object.

21. The apparatus of claim 12 where the computer controls the digital micromirror, camera and variable filter to determine severity of bruising in the food object by quantitative assessment of the mean scattering coefficient of a bruised region.

22. The apparatus of claim 12 where the apparatus is arranged and configured to be field deployable to assess the food object in the field.

* * * * *